United States Patent [19]
Ito et al.

[11] Patent Number: 5,395,832
[45] Date of Patent: Mar. 7, 1995

[54] BENZAMIDE DERIVATIVES

[75] Inventors: Yasuo Ito, Katsuyama; Hideo Kato, Fukui; Shingo Yasuda, Katsuyama; Nobuhiko Iwasaki, Katsuyama; Hiroyuki Nishino, Katsuyama; Makoto Takeshita, Katsuyama, all of Japan

[73] Assignee: Hokuriku Seiyaku Co., Ltd., Katsuyama, Japan

[21] Appl. No.: 104,095

[22] PCT Filed: Feb. 12, 1992

[86] PCT No.: PCT/JP92/00134
§ 371 Date: Aug. 11, 1993
§ 102(e) Date: Aug. 11, 1993

[87] PCT Pub. No.: WO92/14705
PCT Pub. Date: Sep. 3, 1992

[30] Foreign Application Priority Data
Feb. 15, 1991 [JP] Japan .................................. 3-042425
Aug. 22, 1991 [JP] Japan ...................................... 233756

[51] Int. Cl.$^6$ .................... A61K 31/46; A61K 31/44; C07D 451/04; C07D 451/14
[52] U.S. Cl. ...................................... 514/214; 514/299; 514/304; 514/413; 540/585; 546/112; 546/124; 546/130; 546/183; 548/452
[58] Field of Search ............... 546/112, 124, 130, 183; 548/452; 540/585; 514/214, 299, 304, 413

[56] References Cited
U.S. PATENT DOCUMENTS

| | | | |
|---|---|---|---|
| 4,163,789 | 8/1979 | Mauri et al. | 546/234 |
| 4,808,624 | 2/1989 | Monkovie et al. | 514/523 |
| 4,877,780 | 10/1989 | Vega-Noverola et al. | 514/161 |

FOREIGN PATENT DOCUMENTS

| | | |
|---|---|---|
| 0013138 | 7/1980 | European Pat. Off. . |
| 52-122379 | 10/1977 | Japan . |
| 55-092384 | 7/1980 | Japan . |
| 58-10578 | 1/1983 | Japan . |
| 61-63642 | 4/1986 | Japan . |
| 1-50883 | 2/1989 | Japan . |

*Primary Examiner*—Bernard Dentz
*Attorney, Agent, or Firm*—Cushman, Darby & Cushman

[57] ABSTRACT

A benzamide derivative represented by the following formula:

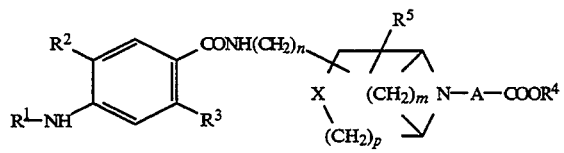

wherein $R^1$ represents a hydrogen atom or a lower alkanoyl group; $R^2$ represents a hydrogen atom or a halogen atom; $R^3$ represents a lower alkoxy group; $R^4$ represents a hydrogen atom or a lower alkyl group; $R^5$ represents a hydrogen atom, a lower alkyl group, or a lower alkoxy group; A represents $C_1$-$C_7$ alkylene group which may optionally be substituted with a lower alkyl group; X represents a methylene group, an oxygen atom, or a sulfur atom; m represents an integer of from 0 to 3; n represents an integer of from 0 to 3; and p represents an integer of from 0 to 2 and a pharmacologically acceptable salt thereof is provided. These compounds are useful since they have gastrointestinal stimulating activity, and a pharmaceutical composition comprising said compound is useful for the treatment of gastrointestinal diseases.

12 Claims, No Drawings

BENZAMIDE DERIVATIVES

TECHNICAL FIELD

The present invention relates to novel benzamide derivatives which have excellent gastrointestinal stimulating activity and antiemetic activity and are useful as medicament for the treatment of gastrointestinal diseases. The present invention further relates to a method for preparing said benzamide derivatives and a pharmaceutical composition useful for the treatment of gastrointestinal diseases comprising said benzamide derivative as an active ingredient.

BACKGROUND ART

Since the development of Metoclopramide (The Merck Index, 11th Edition, 6063) as an antiemetic agent and a gastrointestinal prokinetic agent, various substituted benzamide derivatives having antiemetic activity and gastrointestinal stimulating activity have been provided.

For example, The Merck Index (11th edition, 2344) discloses Clebopride which is a benzamide derivative having a piperidine ring and is useful as antiulcer agent. The Merck Index (11th edition, 2318) discloses Cisapride useful as a gastrointestinal prokinetic agent. These drugs are widely used clinically. In addition, Japanese Patent Unexamined Publication No. (Sho)55-92384 discloses that benzamide derivatives substituted with an azabicyclo ring have antiemetic activity and gastrointestinal stimulating activity and that they are useful as an antiemetic agent and a gastrointestinal prokinetic agent.

However, these substituted benzamide derivatives are not sufficiently useful since they do not have stimulating activity on lower digestive tracts such as the large intestine, although they have stimulating activity on upper digestive tracts such as the stomach. Furthermore, these substituted benzamide derivatives are not satisfactory from a safe standpoint since they sometimes cause adverse reactions such as extrapyramidal syndrome or hyperprolactinemia.

Accordingly, an object of the present invention is to provide medicament for the treatment of gastrointestinal diseases having stimulating activity not only on upper digestive tract but on lower digestive tract and reduced side effects.

The inventors of the present invention conducted various studies to achieve the aforementioned object, and found that novel benzamide derivatives of the present invention have stimulating activity both on upper digestive tract and lower digestive tract. The inventors also found that these novel benzamide derivatives have reduced side effects and are useful as medicament for the treatment of gastrointestinal diseases having excellent selectivity. The present invention was achieved on the basis of these findings.

DISCLOSURE OF THE INVENTION

The present invention provides benzamide derivatives represented by the following formula (I):

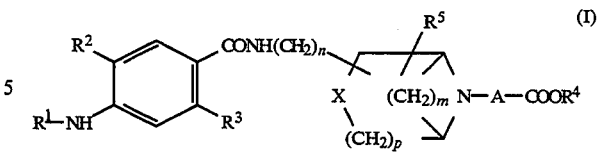

wherein, $R^1$ represents a hydrogen atom or a lower alkanoyl group; $R^2$ represents a hydrogen atom or a halogen atom; $R^3$ represents a lower alkoxy group; $R^4$ represents a hydrogen atom or a lower alkyl group; $R^5$ represents a hydrogen atom, a lower alkyl group, or a lower alkoxy group; A represents $C_1$–$C_7$ alkylene group which may optionally be substituted with a lower alkyl group; X represents a methylene group, an oxygen atom, or a sulfur atom; m represents an integer of from 0 to 3; n represents an integer of from 0 to 3; and p represents an integer of from 0 to 2, or pharmacologically acceptable salts thereof. The benzamide derivatives are useful since they have gastrointestinal stimulating activity.

According to another embodiment of the present invention, a method for preparing said benzamide derivatives is provided.

According to yet another embodiment of the present invention, a pharmaceutical composition useful for the treatment of gastrointestinal diseases which comprises said benzamide derivative as an active ingredient. The pharmaceutical composition is useful as, for example, a gastrointestinal prokinetic agent, an antiemetic agent, an agent for the treatment of irritable bowel syndrome, and agent for the treatment of constipation.

BEST MODE FOR CARRYING OUT THE INVENTION

In the aforementioned formula (I), a lower alkanoyl group represented by $R^1$ may be, for example, formyl group, acetyl group, propanoyl group, butyroyl group, or trimethylacetyl group. A halogen atom represented by $R^2$ may be, for example, a fluorine atom, a chlorine atom, or a bromine atom. A lower alkoxy group represented by $R^3$ and $R^5$ may be, for example, methoxy group, ethoxy group, propoxy group, isopropoxy group, butoxy group, isobutoxy group, or tert-butoxy group. A lower alkyl group represented by $R^4$ and $R^5$ or a lower alkyl group which may optionally substitute on the alkylene group represented by A may be, for example, methyl group, ethyl group, n-propyl group, isopropyl group, n-butyl group, or tert-butyl group. $R^5$ and Ph—$CONH(CH_2)_n$—(wherein Ph represents a substituted phenyl) may substitute at any position of a ring comprising X and N.

Examples of pharmacologically acceptable salts of the benzamide drivatives of the present invention include alkali-addition salts or acid-addition salts. Examples of the alkali-addition salts include, for example, inorganic alkali-addition salts such as, for example, sodium salt, potassium salt, calcium salt, and ammonium salt, and organic base-addition salts such as, for example, ethylenediamine salt, ethanolamine salt, N,N-dialkylethanolamine salt, and triethanolamine salt. Examples of the acid addition salts include, for example, inorganic acid-addition salts such as, for example, hydrochloride, hydrobromide, hydroiodide, sulfate, nitrate, and phosphate, and organic acid-addition salts such as, for example, acetate, maleate, fumarate, citrate, oxalate, tartrate, malate, mandelate, methanesulfonate, p-toluenesulfonate, and 10-camphorsulfonate.

The benzamide derivatives of the present invention represented by the above-described formula (I) may optionally have an asymmetric carbon atom. Each of enantio-isomers distinguished by the asymmetric carbon atom, an arbitrary mixture thereof, and racemate, i.e., equimolor mixture thereof, fall within the scope of the present invention. Where the benzamide derivatives of the present invention have more than one asymmetric carbon atoms, each diastereomer and an arbitrary mixture of the diastereomers also fall within the scope of the present invention.

The benzamide derivatives of the present invention may be in any one of possible conformations. For instance, where the compounds of the aforementioned formula (I) wherein p is 1, piperidine, morphorine, or thiamorphorine ring substituted with Ph—CONH(CH$_2$)$_n$—group may be in any one of configurations selected from chair form, boat form, or twist-boat form. In the specification, compounds having Ph—CONH(CH$_2$)$_n$—group and —(CH$_2$)$_m$—cross linking group above the same side of a ring plane comprising X and N are referred to as endo-compounds, and compounds having each of the groups above the opposite sides of the plane are referred to as exo-compounds.

Preferred embodiments of the benzamide derivatives of the present invention include the following compounds:

(1) ethyl exo-[3-(4-acetylamino-2-methoxybenzamido)-8-azabicyclo[3.2.1]oct-8-yl]acetate;
(2) ethyl exo-4-[3-(4-acetylamino-2-methoxybenzamido)-8-azabicyclo[3.2.1]oct-8-yl]butyrate;
(3) ethyl endo-[3-(4-acetylamino-2-methoxybenzamido)-8-azabicyclo[3.2.1]oct-8-yl]acetate;
(4) ethyl endo-4-[3-(4-acetylamino-2-methoxybenzamido)-8-azabicyclo[3.2.1]oct-8-yl]butyrate;
(5) ethyl exo-[3-(4-acetylamino-2-methoxybenzamido)-9-azabicyclo[3.3.1]non-9-yl]acetate;
(6) ethyl exo-4-[3-(4-acetylamino-2-methoxybenzamido)-9-azabicyclo[3.3.1]non-9-yl]butyrate;
(7) ethyl endo-[3-(4-acetylamino-2-methoxybenzamido)-9-azabicyclo[3.3.1]non-9-yl]acetate;
(8) ethyl endo-3-[3-(4-acetylamino-2-methoxybenzamido)-9-azabicyclo[3.3.1]non-9-yl]propionate;
(9) ethyl endo-4-[3-(4-acetylamino-2-methoxybenzamido)-9-azabicyclo[3.3.1]non-9-yl]butyrate;
(10) ethyl endo-5-[3-(4-acetylamino-2-methoxybenzamido)-9-azabicyclo[3.3.1]non-9-yl]valerate;
(11) methyl endo-6-[3-(4-acetylamino-2-methoxybenzamido)-9-azabicyclo[3.3.1]non-9-yl]hexanoate;
(12) methyl endo-7-[3-(4-acetylamino-2-methoxybenzamido)-9-azabicyclo[3.3.1]non-9-yl]heptanoate;
(13) methyl endo-8-[3-(4-acetylamino-2-methoxybenzamido)-9-azabicyclo[3.3.1]non-9-yl]octanoate;
(14) ethyl endo-[3-(4-acetylamino-2-ethoxybenzamido)-9-azabicyclo[3.3.1]non-9-yl]acetate;
(15) ethyl endo-4-[3-(4-acetylamino-2-ethoxybenzamido)-9-azabicyclo[3.3.1]non-9-yl]butyrate;
(16) ethyl exo-[3-(4-acetylamino-5-chloro-2-methoxybenzamido)-8-azabicyclo[3.2.1]oct-8-yl]acetate;
(17) ethyl exo-4-[3-(4-acetylamino-5-chloro-2-methoxybenzamido)-8-azabicyclo[3.2.1]oct-8-yl]butyrate;
(18) ethyl endo-[3-(4-acetylamino-5-chloro-2-methoxybenzamido)-8-azabicyclo[3.2.1]oct-8-yl]acetate;
(19) ethyl endo-4-[3-(4-acetylamino-5-chloro-2-methoxybenzamido)-8-azabicyclo[3.2.1]oct-8-yl]butyrate;
(20) ethyl exo-[3-(4-acetylamino-5-chloro-2-methoxybenzamido)-9-azabicyclo[3.3.1]non-9-yl]acetate;
(21) ethyl exo-4-[3-(4-acetylamino-5-chloro-2-methoxybenzamido)-9-azabicyclo[3.3.1]non-9-yl]butyrate;
(22) ethyl endo-[3-(4-acetylamino-5-chloro-2-methoxybenzamido)-9-azabicyclo[3.3.1]non-9-yl]acetate;
(23) ethyl endo-3-[3-(4-acetylamino-5-chloro-2-methoxybenzamido)-9-azabicyclo[3.3.1]non-9-yl]propionate;
(24) ethyl endo-4-[3-(4-acetylamino-5-chloro-2-methoxybenzamido)-9-azabicyclo[3.3.1]non-9-yl]butyrate;
(25) ethyl endo-5-[3-(4-acetylamino-5-chloro-2-methoxybenzamido)-9-azabicyclo[3.3.1]non-9-yl]valerate;
(26) methyl endo-6-[3-(4-acetylamino-5-chloro-2-methoxybenzamido)-9-azabicyclo[3.3.1]non-9-yl]hexanoate;
(27) methyl endo-7-[3-(4-acetylamino-5-chloro-2-methoxybenzamido)-9-azabicyclo[3.3.1]non-9-yl]heptanoate;
(28) methyl endo-8-[3-(4-acetylamino-5-chloro-2-methoxybenzamido)-9-azabicyclo[3.3.1]non-9-yl]octanoate;
(29) ethyl endo-[3-(4-acetylamino-5-chloro-2-ethoxybenzamido)-9-azabicyclo[3.3.1]non-9-yl]acetate;
(30) ethyl endo-4-[3-(4-acetylamino-5-chloro-2-ethoxybenzamido)-9-azabicyclo[3.3.1]non-9-yl]butyrate;
(31) ethyl exo-[3-(4-amino-5-chloro-2-methoxybenzamido)-8-azabicyclo[3.2.1]oct-8-yl]acetate;
(32) ethyl exo-4-[3-(4-amino-5-chloro-2-methoxybenzamido)-8-azabicyclo[3.2.1]oct-8-yl]butyrate;
(33) ethyl endo-[3-(4-amino-5-chloro-2-methoxybenzamido)-8-azabicyclo[3.2.1]oct-8-yl]acetate;
(34) ethyl endo-4-[3-(4-amino-5-chloro-2-methoxybenzamido)-8-azabicyclo[3.2.1]oct-8-yl]butyrate;
(35) ethyl exo-[3-(4-amino-5-chloro-2-methoxybenzamido)-9-azabicyclo[3.3.1]non-9-yl]acetate;
(36) ethyl exo-4-[3-(4-amino-5-chloro-2-methoxybenzamido)-9-azabicyclo[3.3.1]non-9-yl]butyrate;
(37) ethyl endo-[3-(4-amino-5-chloro-2-methoxybenzamido)-9-azabicyclo[3.3.1]non-9-yl]acetate;
(38) ethyl endo-3-[3-(4-amino-5-chloro-2-methoxybenzamido)-9-azabicyclo[3.3.1]non-9-yl]propionate;
(39) ethyl endo-2-[3-(4-amino-5-chloro-2-methoxybenzamido)-9-azabicyclo[3.3.1]non-9-yl]propionate;
(40) ethyl endo-4-[3-(4-amino-5-chloro-2-methoxybenzamido)-9-azabicyclo[3.3.1]non-9-yl]butyrate;
(41) ethyl endo-5-[3-(4-amino-5-chloro-2-methoxybenzamido)-9-azabicyclo[3.3.1]non-9-yl]valerate;
(42) ethyl endo-6-[3-(4-amino-5-chloro-2-methoxybenzamido)-9-azabicyclo[3.3.1]non-9-yl]hexanoate;
(43) methyl endo-7-[3-(4-amino-5-chloro-2-methoxybenzamido)-9-azabicyclo[3.3.1]non-9-yl]heptanoate;
(44) ethyl endo-8-[3-(4-amino-5-chloro-2-methoxybenzamido)-9-azabicyclo[3.3.1]non-9-yl]octanoate;
(45) ethyl endo-[3-(4-amino-5-chloro-2-ethoxybenzamido)-9-azabicyclo[3.3.1]non-9-yl]acetate;
(46) ethyl endo-4-[3-(4-amino-5-chloro-2-ethoxybenzamido)-9-azabicyclo[3.3.1]non-9-yl]butyrate;
(47) ethyl endo-[3-[(4-amino-5-chloro-2-methoxybenzamido)methyl]-9-azabicyclo[3.3.1]non-9-yl]acetate;
(48) ethyl endo-4-[3-[(4-amino-5-chloro-2-methoxybenzamido)methyl]-9-azabicyclo[3.3.1]non-9-yl]butyrate;
(49) ethyl endo-[3-[2-(4-amino-5-chloro-2-methoxybenzamido)ethyl]-9-azabicyclo[3.3.1]non-9-yl]acetate;
(50) ethyl endo-4-[3-[2-(4-amino-5-chloro-2-methoxybenzamido)ethyl]-9-azabicyclo[3.3.1]non-9-yl]butyrate;
(51) ethyl endo-[3-[3-(4-amino-5-chloro-2-methoxybenzamido)propyl]-9-azabicyclo[3.3.1]non-9-yl]acetate;

(52) ethyl endo-4-[3-[3-(4-amino-5-chloro-2-methoxybenzamido)-propyl]-9-azabicyclo[3.3.1]non-9-yl]butyrate;
(53) exo-[3-(4-amino-5-chloro-2-methoxybenzamido)-8-azabicyclo[3.2.1]oct-8-yl]acetic acid;
(54) exo-4-[3-(4-amino-5-chloro-2-methoxybenzamido)-8-azabicyclo[3.2.1]oct-8-yl]butyric acid;
(55) endo-[3-(4-amino-5-chloro-2-methoxybenzamido)-8-azabicyclo[3.2.1]oct-8-yl]acetic acid;
(56) endo-4-[3-(4-amino-5-chloro-2-methoxybenzamido)-8-azabicyclo[3.2.1]oct-8-yl]butyric acid;
(57) exo-[3-(4-amino-5-chloro-2-methoxybenzamido)-9-azabicyclo[3.3.1]non-9-yl]acetic acid;
(58) exo-4-[3-(4-amino-5-chloro-2-methoxybenzamido)-9-azabicyclo[3.3.1]non-9-yl]butyric acid;
(59) endo-[3-(4-amino-5-chloro-2-methoxybenzamido)-9-azabicyclo[3.3.1]non-9-yl]acetic acid;
(60) endo-3-[3-(4-amino-5-chloro-2-methoxybenzamido)-9-azabicyclo[3.3.1]non-9-yl]propionic acid;
(61) endo-2-[3-(4-amino-5-chloro-2-methoxybenzamido)-9-azabicyclo[3.3.1]non-9-yl]propionic acid;
(62) endo-4-[3-(4-amino-5-chloro-2-methoxybenzamido)-9-azabicyclo[3.3.1]non-9-yl]butyric acid;
(63) endo-5-[3-(4-amino-5-chloro-2-methoxybenzamido)-9-azabicyclo[3.3.1]non-9-yl]valeric acid;
(64) endo-6-[3-(4-amino-5-chloro-2-methoxybenzamido)-9-azabicyclo[3.3.1]non-9-yl]hexanoic acid;
(65) endo-7-[3-(4-amino-5-chloro-2-methoxybenzamido)-9-azabicyclo[3.3.1]non-9-yl]heptanoic acid;
(66) endo-8-[3-(4-amino-5-chloro-2-methoxybenzamido)-9-azabicyclo[3.3.1]non-9-yl]octanoic acid;
(67) endo-[3-(4-amino-5-chloro-2-ethoxybenzamido)-9-azabicyclo[3.3.1]non-9-yl]acetic acid;
(68) endo-4-[3-(4-amino-5-chloro-2-ethoxybenzamido)-9-azabicyclo[3.3.1]non-9-yl]butyric acid;
(69) endo-[3-[(4-amino-5-chloro-2-methoxybenzamido)-methyl]-9-azabicyclo[3.3.1]non-9-yl]acetic acid;
(70) endo-4-[3-[(4-amino-5-chloro-2-methoxybenzamido)methyl]-9-azabicyclo[3.3.1]non-9-yl]butyric acid;
(71) endo-[3-[2-(4-amino-5-chloro-2-methoxybenzamido)ethyl]-9-azabicyclo[3.3.1]non-9-yl]acetic acid;
(72) endo-4-[3-[2-(4-amino-5-chloro-2-methoxybenzamido)ethyl]-9-azabicyclo[3.3.1]non-9-yl]butyric acid;
(73) endo-[3-[3-(4-amino-5-chloro-2-methoxybenzamido)propyl]-9-azabicyclo[3.3.1]non-9-yl]acetic acid;
(74) endo-4-[3-[3-(4-amino-5-chloro-2-methoxybenzamido)propyl]-9-azabicyclo[3.3.1]non-9-yl]butyric acid;
(75) ethyl [4-(4-amino-5-chloro-2-methoxybenzamido)-piperidino]acetate;
(76) ethyl 2-[4-(4-amino-5-chloro-2-methoxybenzamido)piperidino]propionate;
(77) ethyl 3-[4-(4-amino-5-chloro-2-methoxybenzamido)piperidino]propionate;
(78) ethyl 4-[4-(4-amino-5-chloro-2-methoxybenzamido)piperidino]butyrate;
(79) ethyl 5-[4-(4-amino-5-chloro-2-methoxybenzamido)piperidino]valerate;
(80) methyl 6-[4-(4-amino-5-chloro-2-methoxybenzamido)piperidino]hexanoate;
(81) ethyl [4-[(4-amino-5-chloro-2-methoxybenzamido)-methyl]piperidino]acetate;
(82) ethyl 4-[4-[(4-amino-5-chloro-2-methoxybenzamido)methyl]piperidino]butyrate;
(83) ethyl [4-[2-(4-amino-5-chloro-2-methoxybenzamido)ethyl]piperidino]acetate;
(84) ethyl 4-[4-[2-(4-amino-5-chloro-2-methoxybenzamido)ethyl]piperidino]butyrate;
(85) ethyl [4-[3-(4-amino-5-chloro-2-methoxybenzamido)propyl]piperidino]acetate;
(86) ethyl 4-[4-[3-(4-amino-5-chloro-2-methoxybenzamido)propyl]piperidino]butyrate;
(87) [4-(4-amino-5-chloro-2-methoxybenzamido)-piperidino]acetic acid;
(88) 2-[4-(4-amino-5-chloro-2-methoxybenzamido)-piperidino]propionic acid;
(89) 3-[4-(4-amino-5-chloro-2-methoxybenzamido)-piperidino]propionic acid;
(90) 4-[4-(4-amino-5-chloro-2-methoxybenzamido)-piperidino]butyric acid;
(91) 5-[4-(4-amino-5-chloro-2-methoxybenzamido)-piperidino]valeric acid;
(92) 6-[4-(4-amino-5-chloro-2-methoxybenzamido)-piperidino]hexanoic acid;
(93) [4-[(4-amino-5-chloro-2-methoxybenzamido)methyl]piperidino]acetic acid;
(94) 4-[4-[(4-amino-5-chloro-2-methoxybenzamido)methyl]piperidino]butyric acid;
(95) [4-[2-(4-amino-5-chloro-2-methoxybenzamido)ethyl]piperidino]acetic acid;
(96) 4-[4-[2-(4-amino-5-chloro-2-methoxybenzamido)ethyl]piperidino]butyric acid;
(97) [4-[3-(4-amino-5-chloro-2-methoxybenzamido)-propyl]piperidino]acetic acid;
(98) 4-[4-[3-(4-amino-5-chloro-2-methoxybenzamido)-propyl]piperidino]butyric acid;
(99) ethyl cis-[4-(4-amino-5-chloro-2-methoxybenzamido)-3-methoxypiperidino]acetate;
(100) ethyl trans-[4-(4-amino-5-chloro-2-methoxybenzamido)-3-methoxypiperidino]acetate;
(101) ethyl cis-4-[4-(4-amino-5-chloro-2-methoxybenzamido)-3-methoxypiperidino]butyrate;
(102) ethyl trans-4-[4-(4-amino-5-chloro-2-methoxybenzamido)-3-methoxypiperidino]butyrate;
(103) methyl cis-6-[4-(4-amino-5-chloro-2-methoxybenzamido)-3-methoxypiperidino]hexanoate;
(104) ethyl cis-[4-(4-amino-5-chloro-2-methoxybenzamido)-3-methylpiperidino] acetate;
(105) ethyl trans-[4-(4-amino-5-chloro-2-methoxybenzamido)-3-methylpiperidino]acetate;
(106) ethyl cis-4-[4-(4-amino-5-chloro-2-methoxybenzamido)-3-methylpiperidino]butyrate;
(107) ethyl trans-4-[4-(4-amino-5-chloro-2-methoxybenzamido)-3-methylpiperidino]butyrate;
(108) methyl cis-6-[4-(4-amino-5-chloro-2-methoxybenzamido)-3-methylpiperidino]hexanoate;
(109) cis-[4-(4-amino-5-chloro-2-methoxybenzamido)-3-methoxypiperidino]acetic acid;
(110) trans-[4-(4-amino-5-chloro-2-methoxybenzamido)-3-methoxypiperidino]acetic acid;
(111) cis-4-[4-i.4-amino-5-chloro-2-methoxybenzamido)-3-methoxypiperidino]butyric acid;
(112) trans-4-[4-(4-amino-5-chloro-2-methoxybenzamido)-3-methoxypiperidino]butyric acid;
(113) cis-6-[4-(4-amino-5-chloro-2-methoxybenzamido)-3-methoxypiperidino]hexanoic acid;
(114) cis-[4-(4-amino-5-chloro-2-methoxybenzamido)-3-methylpiperidino]butyric acid;
(115) trans-[4-(4-amino-5-chloro-2-methoxybenzamido)-3-methylpiperidino]acetic acid;
(116) cis-4-[4-(4-amino-5-chloro-2-methoxybenzamido)-3-methylpiperidino]butyric acid;
(117) trans-4-[4-(4-amino-5-chloro-2-methoxybenzamido)-3-methylpiperidino] butyric acid;

(118) cis-6-[4-(4-amino-5-chloro-2-methoxybenzamido)-3-methylpiperidino]hexanoic acid;
(119) ethyl [2-[(4-amino-5-chloro-2-methoxybenzamido)methyl]morpholino]acetate;
(120) ethyl 4-[2-[(4-amino-5-chloro-2-methoxybenzamido)methyl]morpholino]butyrate;
(121) [2-[(4-amino-5-chloro-2-methoxybenzamido)methyl]morpholino]acetic acid;
(122) 4-[2-[(4-amino-5-chloro-2-methoxybenzamido)methyl]morpholino]butyric acid;
(123) ethyl [2-[(4-amino-5-chloro-2-methoxybenzamido)methyl]thiamorpholino]acetate;
(124) ethyl 4-[2-[(4-amino-5-chloro-2-methoxybenzamido)methyl]thiamorpholino]butyrate;
(125) [2-[(4-amino-5-chloro-2-methoxybenzamido)methyl]thiamorpholino]acetic acid;
(126) 4-[2-[(4-amino-5-chloro-2-methoxybenzamido)methyl]thiamorpholino]butyric acid;
(127) ethyl [3-[(4-amino-5-chloro-2-methoxybenzamido)methyl]pyrrolidin-1-yl]acetate;
(128) ethyl 4-[3-[(4-amino-5-chloro-2-methoxybenzamido)methyl]pyrrolidin-1-yl]butyrate;
(129) [3-[(4-amino-5-chloro-2-methoxybenzamido)methyl]pyrrolidin-1-yl]acetic acid;
(130) 4-[3-[(4-amino-5-chloro-2-methoxybenzamido)methyl]pyrrolidin- 1-yl]butyric acid;
(131) ethyl [3-(4-amino-5-chloro-2-methoxybenzamido)pyrrolidin-1-yl]acetate;
(132) ethyl 4-[3-(4-amino-5-chloro-2-methoxybenzamido)pyrrolidin-1-yl]butyrate;
(133) [3-(4-amino-5-chloro-2-methoxybenzamido)pyrrolidin-1-yl]acetic acid; and
(134) 4-[3-(4-amino-5-chloro-2-methoxybenzamido)pyrrolidin-1-yl]butyric acid. However, the present invention is not limited to these examples.

The benzamide derivative represented by formula (I) can be prepared according to a method described below which is an embodiment of the present invention. However, methods for preparing said compound are not limited to these processes.

A process for preparing the benzamide derivatives of the present invention represented by formula (I) comprises the following steps:

(a) reacting a compound represented by the following formula (II) wherein $R^1$, $R^2$, $R^3$, $R^5$, X, m, n, and p are the same as those defined above:

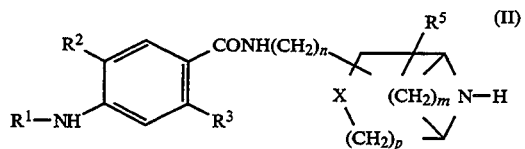

with a compound represented by the following formula (III) wherein A is the same as that defined above, $R^6$ represents a lower alkyl, and Y represents a halogen atom:

$$Y-A-CO_2R^6 \text{ or } CH=CH_2CO_2R^6 \quad (III)$$

to carry out N-alkylation reaction in an organic solvent or without a solvent and in the presence or absence of a base as a dehydrohalogenating agent; and (b) halogenating or hydrolyzing the product obtained in the above step (a), if desired.

Examples of the organic solvent used for the N-alkylation in the method of the present invention include, for example, alcohols such as, for example, methanol, ethanol, n-propanol, isopropanol, and n-butanol; aromatic hydrocarbons such as, for example, benzene, toluene, and xylene; and aprotic polar solvents such as, for example, tetrahydrofuran, 1,4-dioxane, acetonitrile, N,N-dimethylformamide, N-methyl-2-pyrrolidone, and dimethyl sulfoxide. Examples of the base used include, for example, metallic sodium, sodium hydride, sodium methoxide, sodium ethoxide, sodium amide, sodium hydroxide, potassium hydroxide, sodium carbonate, potassium carbonate, sodium hydrogen carbonate, and potassium hydrogen carbonate. The reaction may be carried out at from ice-cooling temperature to refluxing temperature of a solvent.

Halogenation may be carried out by the treatment with a halogenating agent in an organic solvent. Examples of the halogenating agent used include, for example, chlorine, bromine, and sulfuryl chloride. Examples of the organic solvent used include, for example, alcohols such as, for example, methanol, ethanol, and n-propanol; halogenated hydrocarbons such as, for example, dichloromethane, chloroform, carbon tetrachloride, and 1,2-dichloroethane; and aliphatic acids such as, for example, acetic acid. The reaction may be carried out at from $-30°$ C. to refluxing temperature of a solvent.

Hydrolysis may be carried out by using an acid or a base. For acidic hydrolysis, acids such as hydrochloric acid or sulfric acid may be used, and for alkaline hydrolysis, bases such as sodium hydroxide, potassium hydroxide, sodium carbonate, or potassium carbonate may be used. These acids and bases may be used in the reaction in a form of aqueous solution, or alternatively, solutions in methanol, ethanol, n-propanol, isopropanol, n-butanol, sec-butanol, or tert-butanol, or solutions in aqueous organic solvents. The reaction may be carried out at from ice-cooling temperature to refluxing temperature of a solvent.

The compounds represented by formula (II) used as starting materials in the aforementioned preparation process of the present invention are novel compounds with a few exceptions. The compounds can be prepared according to the scheme set out below, in which $R^1$, $R^2$, $R^3$, $R^5$, X, m, n, and p are the same as those defined above, $R^7$ represents a lower alkyl group, and Z represents a halogen atom. Specific examples of the preparation process are given as reference examples in Examples which follows.

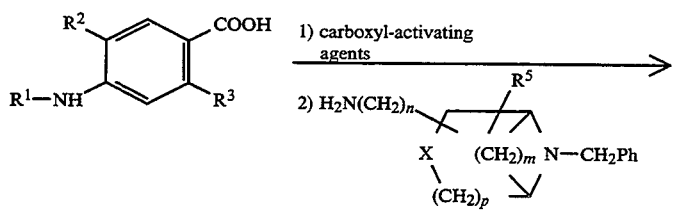

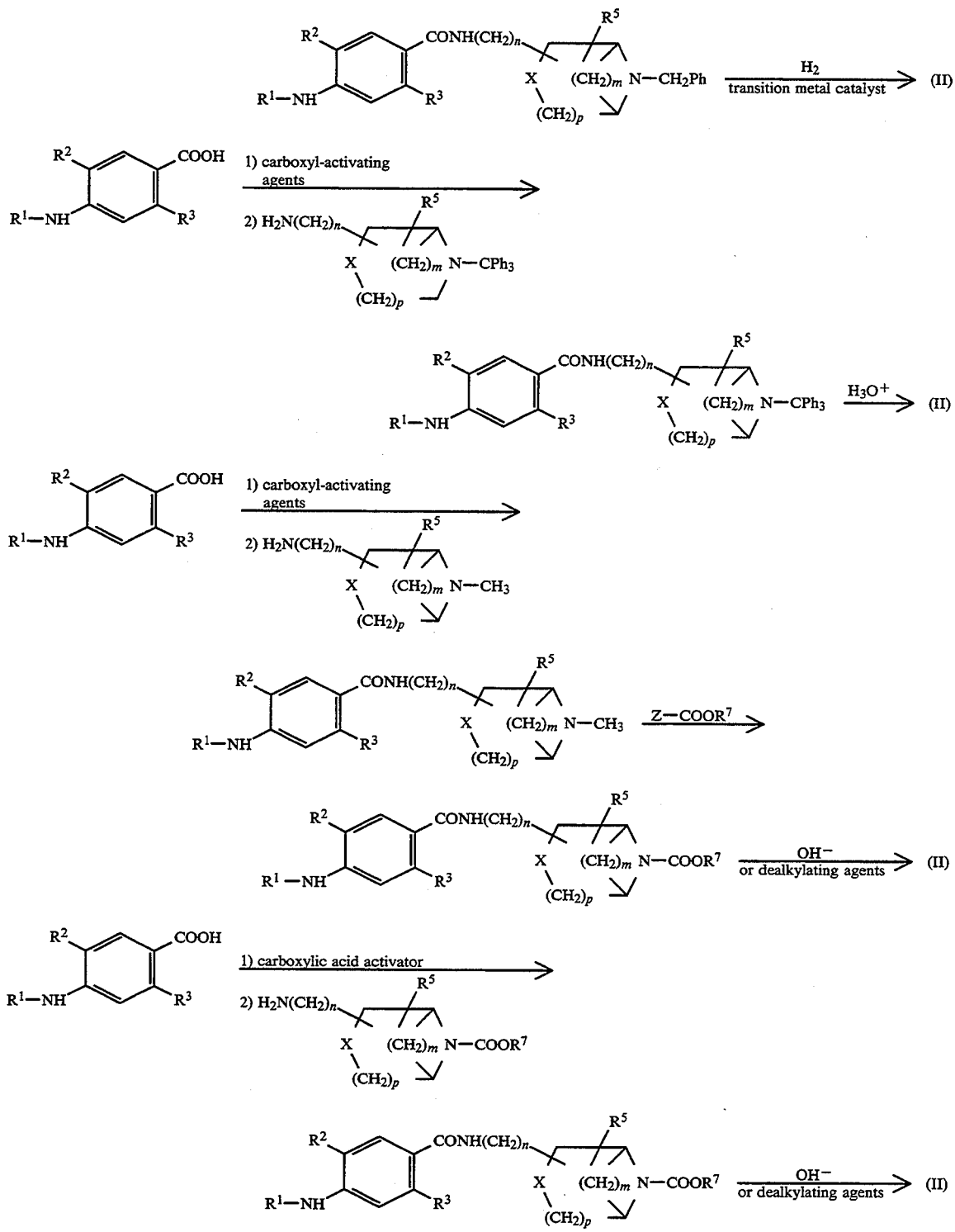

The benzamide derivatives represented by formula (I) prepared according to the process described above and their pharmacologically acceptable salts have hyderfunctional activity on digestive tract and are useful for the treatment of gastrointestinal diseases. The compounds may preferably be formulated in a pharmaceutical composition as an active ingredient. The pharmaceutical composition comprising said compound as an active ingredient may generally be formulated and administered to a patient as orally available compositions such as, for example, capsules, tablets, subtilized granules, granules, powder or syrup, or administered as injection, suppository, eye drop, eye ointment, ear drop, or topical composition.

These pharmaceutical compositions can be prepared by ordinary methods. If necessary, pharmacologically and pharmaceutically acceptable additives may be added. For the preparation of orally available compositions and suppository, excipients such as, for example, lactose, D-mannitol, cornstarch, or crystalline cellulose; disintegrants such as, for example, carboxymethylcellulose or calcium carboxymethylcellulose; binders such as, for example, hydroxypropylcellulose, hydroxypropylmethylcellulose, or polyvinylpyrrolidone; lubricants such as, for example, magnesium stearate or talc; coating agents such as, for example, hydroxypropylmethylcellulose, sucrose, or titanium oxide; or bases such as, for example polyethylene glycol or hard fat may be used as pharmaceutical additives. For the preparation of an injection, eye drop, or ear drop, solubilizing agents or solubilizers such as, for example, distilled water for injection, saline, or propylene glycol which is useful for an aqueous composition or a composition for preparing aqueous solution before use; pH adjusting agents such as, for example, an inorganic or organic acid or base; isotonicity agents such as, for example, sodium chloride, glucose, or glycerin; or stabilizers may be used as pharmaceutical additives. For the preparation of eye ointment and topical composition, suitable pharmaceutical additives ordinarily formulated in ointment, cream, or cataplasms such as white vaseline, macrogol, glycerin, or cloth may be used.

The pharmaceutical compositions of the present invention may be administered orally to an adult patient at a daily dose of about 0.1 to 500 mg. The dose may be increased or decreased depending on the age or conditions of a patient.

As an example demonstrating remarkable advantageous effects of the compounds of the present invention, experimental results are set out below relating to effects on motility of digestive tract of a conscious dog.

Effects on gastrointestinal motility in conscious dog

Under systemical anesthesia, force transducers were chronically implanted to the stomach and the colon of the adult male or female dogs in a direction to measure circular muscle contraction according to the method of Ito et al. (Japanese Journal of Smooth Muscle Research, 13, 33, 1976). A silicone tube chronically attached into jugular vein for intravenous administration of test compounds. After the animal was recovered from the operation, test compounds were administered at about two hours after feeding while gastrointestinal motility was measured. The gastrointestinal motility was indicated as motor index, and the effects of test compounds were estimated by the change of motor index for twenty minutes before and after the administration. The results are summarized in Table 1. It can be concluded that the compounds of the present invention exhibit excellent stimulating effects on lower digestive tracts as well as upper digestive tracts.

TABLE 1

Stimulating Effect on Gastrointestinal Motility (Conscious Dog)

| Test Compound | Dose (mg/kg, i.v.) | Change of Motor Index (%) Stomach | Colon |
|---|---|---|---|
| Example 23 | 1 | 133.5 | 133.3 |
| Example 24 | 0.1 | 116.0 | 134.8 |
| Example 25 | 1 | 180.9 | 132.7 |
| Example 27 | 0.1 | 113.4 | 134.5 |
| Example 28 | 1 | 141.5 | 163.7 |
| Example 32 | 1 | 176.7 | 158.5 |
| Example 33 | 1 | 147.1 | 117.4 |
| Example 34 | 1 | 187.0 | 191.5 |
| Example 35 | 1 | 186.8 | 135.8 |
| Example 36 | 1 | 195.9 | 119.6 |
| Example 38 | 1 | 145.6 | 140.3 |

TABLE 1-continued

Stimulating Effect on Gastrointestinal Motility (Conscious Dog)

| Test Compound | Dose (mg/kg, i.v.) | Change of Motor Index (%) Stomach | Colon |
|---|---|---|---|
| Example 39 | 0.1 | 134.7 | 159.1 |
| Example 41 | 1 | 118.3 | 172.0 |
| Example 43 | 1 | 166.5 | 504.8 |
| Example 46 | 1 | 182.5 | 165.6 |
| Example 58 | 0.1 | 180.7 | 217.5 |
| Example 63 | 1 | 129.6 | 156.6 |
| Example 64 | 0.1 | 200.3 | 234.5 |

The present invention will be explained by way of reference examples and examples. However, the present invention is not limited to these examples.

EXAMPLES

Reference Example 1: endo-4-Acetylamino-N-(9-azabicyclo[3.3.1]non-3-yl)-2-methoxybenzamide (1) endo-4-Acetylamino-N-(9-benzyl-9-azabicyclo[3.3.1]non-3-yl)-2-methoxybenzamide To a mixture of 11.0 g of 4-acetylamino-2-methoxybenzoic acid, 8.5 ml of triethylamine, and 210 ml of tetrahydrofuran, 5.3 ml of ethyl chloroformate was added dropwise with stirring under ice-cooling. After the mixture was stirred for 1.5 hours under ice-cooling, 12.72 g of endo-9-benzyl-9-azabicyclo[3.3.1]nonan-3-amine was added by portions. Stirring was continued for 2.5 days at room temperature, and then the mixture was concentrated under reduced pressure. Water was added to the residue, and pH was adjusted to 9 using 10% aqueous potassium carbonate solution. Crystals precipitated were collected by filtration and washed with water and then with ethanol to give 15.7 g of colorless crystals. Recrystallization from methanol gave colorless needles, m.p. 233.5°–235° C.

Anal. $C_{25}H_{31}N_3O_3$
Calcd. C: 71.23; H: 7.41; N: 9.97
Found C: 71.19; H: 7.50; N: 9.93

(2) endo-4-Acetylamino-N-(9-azabicyclo[3.3.1]non-3-yl)-2-methoxybenzamide

To a mixture of 15.5 g of endo-4-acetylamino-N-(9-benzyl-9-azabicyclo[3.3.1]non-3-yl)-2-methoxybenzamide, 20 ml of acetic acid, and 180 ml of methanol, 2.0 g of Pearlman's catalyst (20% palladium hydroxide on carbon) was added, and then hydrogenolysis was carried out for 1 hour at room temperature under ordinary pressure. The catalyst was removed and the filtrate was concentrated under reduced pressure. The residue was taken up in water and pH was adjusted to 9 by adding potassium carbonate. Crystals precipitated were collected by filtration and washed with water to give 12.6 g of pale yellow crystals. Recrystallization from 1,2-dichloroethane gave colorless prisms, m.p. 196°–200° C.

Anal. $C_{18}H_{25}N_3O_3 \cdot \frac{1}{4}H_2O$
Calcd. C: 64.36; H: 7.65; N: 12.51
Found C: 64.32; H: 7.53; N: 12.47

In the same manner as Reference Example 1, the compounds of Reference Examples 2–4 were obtained.

Reference Example 2: exo-4-Acetylamino-N-(8-azabicyclo[3.2.1]oct-3-yl)-2-methoxybenzamide fumarate (1) exo-4-Acetylamino-N-(8-benzyl-8-azabicyclo[3.2.1]oct-3-yl)-2-methoxybenzamide Appearance: pale brown needles (MeOH)
IR Spectrum ν (KBr) cm$^{-1}$: 1694, 1668
NMR Spectrum δ (DMSO-d$_6$) ppm: 1.50–1.83(6H,m), 1.88–2.14(2H,m), 2.06(3H,s), 3.05–3.32(2H,m), 3.55(2H,s), 3.85(3H,s), 4.05–4.29(1H,m), 7.10–7.45(5H,m), 7.17(1H,dd,J=8.6,1.7Hz), 7.48(1H,d,J=1.7Hz), 7.62–7.77(1H,m), 7.70(1H,d,J=8.6Hz), 10.04(1H,s)

Mass Spectrum m/z: 407 (M+)

(2) exo-4-Acetylamino-N-(8-azabicyclo[3.2.1]oct-3-yl)-2-methoxybenzamide fumarate Appearance: colorless crystals (MeOH)
m.p. 223°–225° C. (decomp.)
Anal. $C_{17}H_{23}N_3O_3 \cdot C_4H_4O_4$
Calcd. C: 58.19; H: 6.28; N: 9.69
Found C: 58.05;.H: 6.45; N: 9.71

Reference Example 3: exo-4-Acetylamino-N-(9-azabicyclo[3.3.1]non-3-yl)-2-methoxybenzamide fumarate (1) exo-4-Acetylamino-N-(9-benzyl-9-azabicyclo[3.3.1]non-3-yl)-2-methoxybenzamide Appearance: slightly brown needles (MeOH)
m.p. 215°–216° C.
Anal. $C_{25}H_{31}N_3O_3$
Calcd. C: 71.23; H: 7.41; N: 9.97
Found C: 71.12; H: 7.48; N: 9.89

(2) exo-4-Acetylamino-N-(9-azabicyclo[3.3.1]non-3-yl)-2-methoxybenzamide fumarate Appearance: colorless crystals (MeOH)
m.p. 194°–196° C. (decomp.)
Anal. $C_{18}H_{25}N_3O_3 \cdot C_4H_4O_4 \cdot \frac{3}{4}H_2O$
Calcd. C: 57.32; H: 6.67; N: 9.12
Found C: 57.13; H: 6.58; N: 9.12

Reference Example 4: endo-4-Acetylamino-N-(9-azabicyclo[3.3.1]non-3-yl)-2-ethoxybenzamide (1) endo-4-Acetylamino-N-(9-benzyl-9-azabicyclo[3.3.1]non-3-yl)-2-ethoxybenzamide Appearance: colorless needles (MeOH)
m.p. 215°–216° C.
Anal. $C_{26}H_{33}N_3O_3$
Calcd. C: 71.70; H: 7.64; N: 9.65
Found C: 71.45; H: 7.61; N: 9.47

(2) endo-4-Acetylamino-N-(9-azabicyclo[3.3.1]non-3-yl)-2-ethoxybenzamide

Appearance: colorless needles (H2O)
m.p. 116°–119° C. 224°–226° C.
Anal. $C_{19}H_{27}N_3O_3 \cdot 5/2H_2O$
Calcd. C: 58.44; H: 8.26; N: 10.76
Found C: 58.45; H: 7.86; N: 10.40

Reference Example 5: endo-4-Acetylamino-N-(8-azabicyclo[3.2.1]oct-3-yl)-5-chloro-2-methoxybenzamide (1) endo-4-Acetylamino-5-chloro-2-methoxy-N-(8-methyl-8-azabicyclo[3.2.1]oct-3-yl)benzamide To a mixture of 38.0 g of 4-acetylamino-5-chloro-2-methoxybenzoic acid, 26.1 ml of triethylamine, and 500 ml of tetrahydrofuran, 15.7 ml of ethyl chloroformate was added dropwise with stirring under ice-cooling. Stirring was continued for 1 hour under ice-cooling, and then a solution of 23.0 g of endo-8-methyl-8-azabicyclo[3.2.1]octan-3-amine in 40 ml of tetrahydrofuran was added dropwise. Stirring was continued for 1.5 hours at room temperature, and then insoluble materials were removed and the filtrate obtained was concentrated under reduced pressure. Water was added to the residue and pH was adjusted to 9 by using aqueous potassium carbonate solution. Crystals precipitated were collected by filtration and Washed with water and then with ethyl acetate to give 48.6 g of slightly yellow crystals.

(2) Methyl endo-[3-(4-acetylamino-5-chloro-2-methoxybenzamido)-8-azabicyclo[3.2.1]oct-8-yl]formate To a mixture of 40.0 g of endo-4-acetylamino-5-chloro-2-methoxy-N-(8-methyl-8-azabicyclo[3.2.1]oct-3-yl)benzamide, 16.0 g of potassium carbonate, and 400 ml of chloroform, 80.0 ml of methyl chloroformate was added dropwise with stirring at room temperature. The mixture was refluxed for 19 hours, and then insoluble materials were removed and the filtrate obtained was concentrated under reduced pressure. The residue was washed with ethyl acetate and then with hot methanol to give 17.5 g of colorless crystals. Recrystallization from dichloromethane-methanol gave colorless needles, m.p. 250°–252° C.

Anal. $C_{19}H_{24}ClN_3O_5 \cdot \frac{1}{2}H_2O$
Calcd. C: 54.48; H: 6.02; N: 10.03
Found C: 54.17; H: 5.77; N: 9.79

(3) endo-4-Acetylamino-N-(8-azabicyclo[3.2.1]oct-3-yl)-5-chloro-2-methoxybenzamide To a suspension of 16.3 g of methyl endo-[3-(4-acetylamino-5-chloro-2-methoxybenzamido)-8-azabicyclo[3.2.1]oct-8-yl]formate in 400 ml of dichloromethane, 22.0 ml of iodo trimethylsilane was added dropwise with stirring at room temperature. Stirring was continued for 6 hours at room temperature, and then aqueous sodium hydrosulfite solution was added. Aqueous layer was separated after pH was adjusted to 2 using 10% hydrochloric acid. The aqueous layer was basified using potassium carbonate and then extracted with dichloromethane. The extract was dried over anhydrous sodium sulfate and concentrated under reduced pressure. The residue was purified using column chromatography on aluminum oxide [eluent: dichloromethane→dichloromethane-methanol (50:1)] to afford 8.41 g of pale yellow syrup.

IR Spectrum $\nu$ (liq) cm$^{-1}$: 1694, 1644

NMR Spectrum $\delta$ (CDCl$_3$) ppm: 1.65–2.30(9H,m), 2.28(3H,s), 3.60–3.74(2H,m), 4.02(3H,s), 4.30–4.46(1H,m), 7.82(1H,br-s), 8.21(1H,s), 8.34(1H,s), 8.40–8.50(1H,m)

High Resolution Mass Spectrum: $C_{17}H_{22}ClN_3O_3$
Calcd. m/z: 351.1350, 353.1320
Found m/z: 351.1363, 353.1325

In the same manner as Reference Example 5, the compound of Reference Example 6 was obtained.

Reference Example 6: endo-4-Acetylamino-N-(9-azabicyclo[3.3.1]non-3-yl)-5-chloro-2-methoxybenzamide (1) endo-4-Acetylamino-5-chloro-2-methoxy-N-(9-methyl-9-azabicyclo[3.3.1]non-3-yl)benzamide Appearance: slightly brown amorphous solid
IR Spectrum $\nu$ (KBr) cm$^{-1}$: 1706, 1646

NMR Spectrum $\delta$ (CDCl$_3$) ppm: 1.00–1.15(2H,m), 1.20–1.40(2H,m), 1.45–1.60(1H,m), 1.85–2.10(3H,m), 2.28(3H,s), 2.40–2.75(2H,m), 2.50(3H,s), 3.00–3.15(2H,m), 3.98(3H,s), 4.35–4.60(1H,m), 7.60–7.70(1H,m), 7.82(1H,br-s), 8.21(1H,s), 8.30(1H,s)

High Resolution Mass Spectrum: $C_{19}H_{26}ClN_3O_3$
Calcd. m/z: 379.1663, 381.1633
Found m/z: 379.1654, 381.1630

(2) Methyl endo-[3-(4-acetylamino-5-chloro-2-methoxybenzamido)-9-azabicyclo[3.3.1]non-9-yl]formate Appearance: colorless crystals (AcOEt)
m.p. 202°–205° C.
Anal. $C_{20}H_{26}ClN_3O_5$ Calcd. C: 56.67; H: 6.18; N: 9.91
Found C: 56.49; H: 6.25; N: 9.69

(3) endo-4-Acetylamino-N-(9-azabicyclo[3.3.1]non-3-yl)-5-chloro-2-methoxybenzamide Appearance: pale yellow syrup
IR Spectrum ν (liq) cm$^{-1}$: 1694, 1646
NMR Spectrum δ (CDCl$_3$) ppm: 1.14–2.00(8H,m), 2.18(1H,br-s), 2.28(3H,s), 2.20–2.40(2H,m), 3.30–3.47(2H,m), 3.99(3H,s), 4.06–4.28(1H,m), 7.57–7.70(1H,m), 7.81(1H,br-s), 8.22(1H, s), 8.32(1H,s)
High Resolution Mass Spectrum: C$_{18}$H$_{24}$ClN$_3$O$_3$
Calcd. m/z: 365.1506, 367.1477
Found m/z: 365.1510, 367.1457

Reference Example 7: endo-4-Amino-N-(8-azabicyclo[3.2.1]oct-3-yl)-5-chloro-2-methoxybenzamide hydrochloride To a solution of 7.86 g of endo-4-acetylamino-N-(8-azabicyclo[3.2.1]oct-3-yl)-5-chloro-2-methoxybenzamide in 23 ml of ethanol, 40 ml of 3.2% hydrogen chloride/ethanol solution was added and then the mixture was refluxed for 5.5 hours. The reaction mixture was concentrated under reduced pressure, and the residue was washed with ethanol to give 5.05 g of pale brown crystals. Recrystallization from methanol gave colorless needles, m.p. 280°–282° C. (decomp.).

Anal. C$_{15}$H$_{20}$ClN$_3$O$_2$ · HCl · ¾H$_2$O
Calcd. C: 50.08; H: 6.30; N: 11.68
Found C: 50.07; H: 6.20; N: 11.57

In the same manner as Reference Example 7, the compound of Reference Example 8 was obtained.

Reference Example 8: endo-4-Amino-N-(9-azabicyclo[3.3.1]non-3-yl)-5-chloro-2-methoxybenzamide hydrochloride Appearance: slightly brown needles (EtOH)
m.p. 257°–261° C. (decomp.)
Anal. C$_{16}$H$_{22}$ClN$_3$O$_2$ · HCl · H$_2$O
Calcd. C: 50.80; H: 6.66; N: 11.11
Found C: 50.74; H: 6.57; N: 10.91

Reference Example 9: 4-Amino-5-chloro-2-methoxy-N-(4-piperidinyl)benzamide hydrochloride (1) 4-Amino-5-chloro-2-methoxy-N-(1-triphenylmethyl-4-piperidinyl)benzamide To a mixture of 16.40 g of 4-amino-5-chloro-2-methoxybenzoic acid, 13.60 ml of triethylamine, and 330 ml of dry tetrahydrofuran, 8.55 ml of ethyl chloroformate was added with stirring under ice-cooling. Stirring was continued for 2 hours under ice-cooling, 30.64 g of 4-amino-1-triphenylmethylpiperidine was added by portions. After stirring was continued for 20 hours at room temperature, insoluble materials were removed and the filtrate obtained was concentrated under reduced pressure. The residue was dissolved in dichloromethane and washed with water. The solution was dried over anhydrous sodium sulfate and then concentrated under reduced pressure. The residue was washed with n-hexane to give 39.42 g of colorless crystals.

IR Spectrum ν (KBr) cm$^{-1}$: 1646, 1624
NMR Spectrum δ (CDCl$_3$) ppm: 1.57–1.81(2H,m), 1.92–2.19(2H,m), 2.73–3.38(2H,m), 3.58–4.08(3H,m), 4.33(2H,br-s), 6.25(1H,s), 7.05–7.55(15H,m), 7.67(1H,br-s), 8.06(1H,s)

(2) 4-Amino-5-chloro-2-methoxy-N-(4-piperidinyl)benzamide hydrochloride

A mixture of 39.42 g of 4-amino-5-chloro-2-methoxy-N-(1-triphenylmethyl-4-piperidinyl)benzamide, 10 ml of concentrated hydrochloric acid, and 600 ml of acetone was refluxed for 40 minutes. After the mixture was cooled to 5° C., crystals precipitated were collected by filtration and washed with acetone to give 25.79 g of colorless crystals, m.p. 165°–168° C.

IR Spectrum ν (KBr) cm$^{-1}$: 2948, 2812, 1640
NMR Spectrum δ (DMSO-d$_6$) ppm: 1.63–1.85(2H,m), 1.92–2.13(2H,m), 2.88–3.09(2H,m), 3.13–3.33(2H,m), 3.83(3H,s), 3.88–4.07(1H,m), 6.53(1H,s), 7.62(1H,s), 7.66–7.79(1H,m)
Mass Spectrum m/z: 283,285 (3:1) [M + (free base)]

In the same manner as Reference Example 9, the compounds of Reference Examples 10 and 11 were obtained.

Reference Example 10: 4-Amino-5-chloro-2-methoxy-N-[(2-morpholinyl)methyl]benzamide hydrochloride (1) 4-Amino-5-chloro-2-methoxy-N-[(4-triphenylmethyl-2-morpholinyl)methyl]benzamide Appearance: slightly brown crystals
NMR Spectrum δ (CDCl$_3$) ppm: 1.35–1.80(2H,m), 2.80–3.10(2H,m), 3.10–3.35(1H,m), 3.50–3.75(1H,m), 3.71(3H,s), 3.75–4.10(3H,m), 4.35(2H,br-s), 6.23(1H,s), 7.05–7.60(15H,m), 7.80–7.90(1H,m), 8.07(1H,s)

(2) 4-Amino-5-chloro-2-methoxy-N-[(2-morpholinyl)methyl]benzamide hydrochloride

Appearance: slightly brown crystals (H$_2$O)
m.p. 219°–222° C.
Anal. C$_{13}$H$_{18}$ClN$_3$O$_3$ · HCl · H$_2$O
Calcd. C: 44.08; H: 5.98; N: 11.86
Found C: 44.20; H: 5.88; N: 11.82

Reference Example 11: 4-Amino-5-chloro-2-methoxy-N-[(3-pyrrolidinyl)-methyl]benzamide hydrochloride (1) 4-Amino-5-chloro-2-methoxy-N-[(1-triphenylmethyl-3-pyrrolidinyl)-methyl]benzamide Appearance: slightly brown crystals
NMR Spectrum δ (CDCl$_3$) ppm: 1.33–1.50(1H,m), 1.50–1.65(1H,m), 1.76–1.96(1H,m), 2.10–2.40(3H,m), 2.46–2.50(1H,m), 3.30–3.60(2H,m), 3.77(3H,s), 4.35(2H,br-s), 6.26(1H,s), 7.05–7.60(15H,m), 7.60–7.75(1H,m), 8.10(1H,s)

(2) 4-Amino-5-chloro-2-methoxy-N-[(3-pyrrolidinyl)-methyl]benzamide hydrochloride Appearance: pale yellow crystals (H$_2$O)
m.p. 204°–206° C.
Anal. C$_{13}$H$_{18}$ClN$_3$O$_2$ · HCl · 5/4H$_2$O
Calcd. C: 45.56; H: 6.32; N: 12.26
Found C: 45.60; H: 6.14; N: 12.30

Reference Example 12: cis-4-Amino-5-chloro-2-methoxy-N-[(3-methoxy-4-piperidinyl)benzamide (1) Ethyl cis-[4-(4-amino-5-chloro-2-methoxybenzamido)-3-methoxypiperidino]formate To a mixture of 33.3 g of 4-amino-5-chloro-3-methoxybenzoic acid, 27.0 ml of triethylamine, and 450 ml of tetrahydrofuran, 16.2 ml of ethyl chloroformate was added dropwise with stirring under ice-cooling. Stirring was continued for 1.5 hours under ice-cooling, a solution of 35.0 g of ethyl cis-(4-amino-3-methoxypiperidino)formate in 50 ml of tetrahydrofuran was added dropwise. After being stirred for 20 hours at room temperature, the reaction mixture was concentrated under reduced pressure. Water was added to the residue, and the mixture was extracted with dichloromethane. The extract was washed with aqueous potassium carbonate solution, dried over anhydrous sodium sulfate, and then concentrated under reduced pressure. The residue was washed with diethyl ether to give 44.5 g of colorless crystals.

(2) cis-4-Amino-5-chloro-2-methoxy-N-[(3-methoxy-4-piperidinyl) benzamide

A mixture of 44.0 g of ethyl cis-[4-(4-amino-5-chloro-2-methoxybenzamide)-3-methoxypiperidino]formate, 67.7 g of potassium hydroxide, and 400 ml of iso-propanol was refluxed for 9 hours. The reaction mixture was concentrated under reduced pressure, and then water was added to the residue and the mixture was extracted with dichloromethane. The extract was dried over anhydrous sodium sulfate and then concentrated under reduced pressure. The residue was washed with iso-propylether to give 27.0 g of colorless crystals. Recrystallization from ethanol gave colorless prisms, m.p. 193°–194° C.

Anal. $C_{14}H_{20}ClN_3O_3$
Calcd. C: 53.59; H: 6.42; N: 13.39
Found C: 53.44; H: 6.38; N: 13.28

Example 1: Ethyl endo-[3-(4-acetylamino-2-methoxybenzamido)-9-azabicyclo[3.3.1]non-9-yl]acetate A mixture of 12.4 g of endo-4-acetylamino-N-(9-azabicyclo[3.3.1]non-3-yl)-2-methoxybenzamide, 4.6 ml of ethyl bromoacetate, 5.72 g of potassium carbonate, and 75 ml of N,N-dimethylformamide was heated for 2 hours at 60° C. with stirring. The reaction mixture was poured into ice-water, and crystals precipitated were collected by filtration and washed with water to give 13.4 g of pale yellow crystals. Recrystallization from benzene gave colorless prisms, m.p. 85°–88° C.

Anal. $C_{22}H_{31}N_3O_5 \cdot \frac{1}{2}H_2O$
Calcd. C: 61.95; H: 7.56; N: 9.85
Found C: 61.85; H: 7.55; N: 9.86

In the same manner as Example 1, the compounds of Examples 2 to 12 were obtained.

Example 2: Ethyl endo-4-[3-(4-acetylamino-2-methoxybenzamido)-9-azabicyclo[3.3.1]non-9-yl]butyrate Appearance: colorless oil
IR Spectrum $\nu$ (liq) cm$^{-1}$: 1732, 1698, 1638
NMR Spectrum $\delta$ (CDCl$_3$) ppm: 1.00–2.15(10H,m), 1.26(3H,t,J=7.0Hz), 2.21(3H,s), 2.37(2H,t,J=7.0Hz), 2.45–2.60(2H,m), 2.60–2.85(2H,m), 3.10–3.30 (2H,m), 3.96(3H,s), 4.13(2H,q,J=7.0Hz), 4.30–4.55(1H,m), 6.77(1H,dd,J=8.5,1.5Hz), 7.65–7.75(1H,m), 7.82(1H,s), 7.86(1H,d,J=1.5Hz), 8.09(1H,d,J=8.5Hz)
High Resolution Mass Spectrum: $C_{24}H_{35}N_3O_5$
Calcd. m/z: 445.2577
Found m/z: 445.2586

Example 3: Methyl endo-6-[3-(4-acetylamino-2-methoxybenzamido)-9-azabicyclo[3.3.1]non-9-yl]hexanoate Appearance: colorless oil
IR Spectrum $\nu$ (liq) cm$^{-1}$: 1738, 1698, 1638
NMR Spectrum $\delta$(CDCl$_3$) ppm: 1.00–2.00(14H,m), 2.21(3H,s), 2.33(2H,t,J=7.5Hz), 2.40–2.65(2H,m), 2.65–2.85(2H,m), 3.15–3.35(2H,m), 3.67(3H,s), 3.97(3H,s), 4.40–4.60(1H,m), 6.78(1H,d,J=8.0Hz), 7.65–7.70(1H,m), 7.70–7.80(1H,m), 7.85(1H,s), 8.10(1H, d, J=8.0Hz )
High Resolution Mass Spectrum: $C_{25}H_{37}N_3O_5$
Calcd. m/z: 459.2733
Found m/z: 459.2744

Example 4: Methyl endo-8-[3-(4-acetylamino-2-methoxybenzamido)-9-azabicyclo[3.3.1]non-9-yl]octanoate Appearance: colorless needles (EtOH)
m.p. 159°–160° C.
IR Spectrum $\nu$ (KBr) cm$^{-1}$: 1740, 1696, 1636
NMR Spectrum $\delta$ (CDCl$_3$) ppm: 1.00–2.15(18H,m), 2.21(3H,s), 2.30(2H,t,J=7.5Hz), 2.40–2.60(2H,m), 2.60–2.70(2H,m), 3.10–3.30(2H,m), 3.67(3H,s), 3.95(3H,s), 4.30–4.60(1H,m), 6.80(1H,dd,J=8.5,2.0Hz), 7.65–7.75(1H,m), 7.87(1H,m), 8.07(1H,d,J=8.5Hz), 8.26(1H,d,J=2.0Hz)
High Resolution Mass Spectrum: $C_{27}H_{41}N_3O_5$
Calcd. m/z: 487.3046
Found m/z: 487.3041

Example 5: Ethyl endo-3-[3-(4-acetylamino-2-methoxybenzamido)-9-azabicyclo[3.3.1]non-9-yl]propionate Appearance: colorless oil
IR Spectrum $\nu$ (KBr) cm$^{-1}$: 1732, 1698, 1638
NMR Spectrum $\delta$ (CDCl$_3$) ppm: 1.00–2.06(8H,m), 1.27(3H,t,J=7.0Hz), 2.21(3H,s), 2.32–2.54(2H,m), 2.40(2H,t,J=7.0Hz), 2.95(2H,t,J=7.0Hz), 3.06–3.20(2H,m), 3.95(3H,s), 4.15(2H,q,J=7.0Hz), 4.28–4.46(1H,m), 6.77(1H,dd,J=8.5,2.0Hz), 7.58–7.72(1H,m), 7.87(1H,br-s), 8.06(1H,d,J=8.5Hz), 8.19(1H,s)
High Resolution Mass Spectrum: $C_{23}H_{33}N_3O_5$
Calcd. m/z: 431.2420
Found m/z: 431.2420

Example 6: Ethyl endo-5-[3-(4-acetylamino-2-methoxybenzamido)-9-azabicyclo[3.3.1]non-9-yl]valerate Appearance: colorless oil
IR Spectrum $\nu$ (KBr) cm$^{-1}$: 1734, 1696, 1636
NMR Spectrum $\delta$ (CDCl$_3$) ppm: 0.95–2.10(12H,m), 1.26(3H,t,J=7.0Hz), 2.21(3H,s), 2.31(2H,t,J=7.0Hz), 2.37–2.55(2H,m), 2.64(2H,t,J=7.0Hz), 3.03–3.20(2H,m), 3.95(3H,s), 4.13(2H,q,J=7.0Hz), 4.33–4.53(1H,m), 6.77(1H,dd,J=8.5,2.0Hz), 7.58–7.72(1H,m), 7.87(1H,d,J=2.0Hz), 8.07(1H,d,J=8.5Hz), 8.09(1H,s)
High Resolution Mass Spectrum: $C_{25}H_{37}N_3O_5$
Calcd. m/z: 459.2733
Found m/z: 459.2724

Example 7: Methyl endo-7-[3-(4-acetylamino-2-methoxybenzamido)-9-azabicyclo[3.3.1]non-9-yl]heptanoate Appearance: colorless oil
IR Spectrum $\nu$ (KBr) cm$^{-1}$: 1732, 1696, 1644
NMR Spectrum $\delta$ (CDCl$_3$) ppm: 1.00–2.10(16H,m), 2.21(3H,s), 2.30(2H,t,J=7.5Hz), 2.37–2.55(2H,m), 2.61(2H,t,J=7.0Hz), 3.05–3.20(2H,m), 3.66(3H,s), 3.93(3H,s), 4.35–4.55(1H,m), 6.84(1H,dd,J=8.5,1.5Hz), 7.64–7.78(1H,m), 7.87(1H,d,J=1.5Hz), 8.03(1H,d,J=8.5Hz), 8.85(1H,s)
High Resolution Mass Spectrum: $C_{26}H_{39}N_3O_5$
Calcd. m/z: 473.2890
Found m/z: 473.2893

Example 8: Ethyl endo-[3-(4-acetylamino-2-ethoxybenzamido)-9-azabicyclo[3.3.1]non-9-yl]acetate Appearance: colorless needles (benzene)
m.p. 77°–81° C.
Anal. $C_{23}H_{33}N_3O_5 \cdot \frac{1}{2}H_2O$
Calcd. C: 62.71; H: 7.78; N: 9.54
Found C: 62.72; H: 7.57; N: 9.55

Example 9: Ethyl exo-[3-(4-acetylamino-2-methoxybenzamido)-9-azabicyclo[3.3.1]non-9-yl]acetate Appearance: colorless oil
IR Spectrum $\nu$ (KBr) cm$^{-1}$: 1746, 1686, 1636
NMR Spectrum $\delta$ (CDCl$_3$) ppm: 1.28(3H,t,J=7.0Hz), 1.40–2.13(10H,m), 2.20(3H,s), 3.00–3.15(2H,m), 3.54(2H,s), 3.94(3H,s), 4.19(2H,q,J=7.0Hz), 4.80–5.00(1H,m), 6.78(1H,dd,J=8.5,2.0Hz), 7.57–7.75(1H,m), 7.83(1H,d,J=2.0Hz), 7.87(1H,s), 8.09(1H,d,J=8.5Hz)

High Resolution Mass Spectrum: $C_{22}H_{31}N_3O_5$
Calcd. m/z: 417.2264
Found m/z: 417.2253

Example 10: Ethyl exo-[3-(4-acetylamino-2-methoxybenzamido)-8-azabicyclo[3.2.1]oct-8-yl]acetate Appearance: pale yellow oil
IR Spectrum $\nu$ (KBr) cm$^{-1}$: 1746, 1692, 1638
NMR Spectrum $\delta$ (CDCl$_3$) ppm: 1.28(3H,t,J=7.0Hz), 1.60–2.10(8H,m), 2.20(3H,s), 3.23(2H,s), 3.30–3.45(2H,m), 3.92(3H,s), 4.20(2H,q,J=7.0Hz), 4.28–4.48(1H,m), 6.77(1H,dd,J=8.5,2.0Hz), 7.60(1H,s), 7.60–7.80(1H,m), 7.80(1H,d,J=2.0Hz), 7.80(1H,s), 8.10(1H,d,J=8.5Hz)

High Resolution Mass Spectrum: $C_{21}H_{29}N_3O_5$
Calcd. m/z: 403.2107
Found m/z: 403.2111

Example 11: Ethyl endo-3-[3-(4-acetylamino-5-chloro-2-methoxybenzamido)-8-azabicyclo[3.2.1]oct-8-yl]acetate Appearance: colorless prisms (EtOH)
m.p. 144°–145° C.
Anal. $C_{21}H_{28}ClN_3O_5$
Calcd. C: 57.60; H: 6.44; N: 9.60
Found C: 57.45; H: 6.32; N: 9.49

Example 12: Ethyl endo-4-[3-(4-amino-5-chloro-2-methoxybenzamido)-8-azabicyclo[3.2.1]oct-8-yl]butyrate Appearance: pale brown needles (AcOEt)
m.p. 154°–156° C.
Anal. $C_{21}H_{30}ClN_3O_4 \cdot \frac{1}{2}H_2O$
Calcd. C: 58.87; H: 7.18; N: 9.81
Found C: 58.80; H: 6.97; N: 9.71

Example 13: Ethyl endo-[3-(4-acetylamino-5-chloro-2-methoxybenzamido)-9-azabicyclo[3.3.1]non-9-yl]acetate To a suspension of 13.0 g of ethyl endo-[3-(4-acetylamino-2-methoxybenzamido)-9-azabicyclo[3.3.1]non-9-yl]acetate in 140 ml of dichloromethane, 3.4 ml of sulfuryl chloride was added dropwise at −10° C. Stirring was continued at room temperature for 1.5 hours, and then the mixture was made basic by adding saturated aqueous sodium bicarbonate solution. The organic layer was separated and dried over anhydrous sodium sulfate. After being concentrated under reduced pressure, the residue was purified by column chromatography on silica gel (eluent: dichloromethane-methanol/50:1) to give 11.4 g of pale yellow amorphous solid.

IR Spectrum $\nu$ (KBr) cm$^{-1}$: 1750, 1646
NMR Spectrum $\delta$ (CDCl$_3$) ppm: 1.05–2.17(8H,m), 1.28(3H,t,J=7.3Hz), 2.28(3H,s), 2.42–2.64(2H,m), 3.12–3.34(2H,m), 3.49(2H,s), 3.98(3H,s), 4.17(2H,q,J=7.3Hz), 4.34–4.55(1H,m), 7.58–7.71(1H,m), 7.80(1H,s), 8.22(1H,s), 8.32(1H,s)

High Resolution Mass Spectrum: $C_{22}H_{30}ClN_3O_5$
Calcd. m/z: 451.1874, 453.1844
Found m/z: 451.1859, 453.1853

In the same manner as Example 13, the compounds of Examples 14 to 22 were obtained.

Example 14: Ethyl endo-4-[3-(4-acetylamino-5-chloro-2-methoxybenzamido)-9-azabicyclo[3.3.1]non-9-yl]butyrate Appearance: colorless oil
IR Spectrum $\nu$ (liq) cm$^{-1}$: 1732, 1704, 1646
NMR Spectrum $\delta$ (CDCl$_3$) ppm: 1.00–2.10(10H,m), 1.27(3H,t,J=7.0Hz), 2.28(3H,s), 2.37(2H,t,J=7.5Hz), 2.45–2.60(2H,m), 2.65–2.80(2H,m), 3.05–3.20(2H,m), 3.98(3H,s), 4.14(2H,q,J=7.0Hz), 4.30–4.50(1H,m), 7.55–7.65(1H,m), 7.82(1H,s), 8.20(1H,s), 8.31(1H,s)

High Resolution Mass Spectrum: $C_{24}H_{34}ClN_3O_5$
Calcd. m/z: 479.2187, 481.2157
Found m/z: 479.2190, 481.2173

Example 15: Methyl endo-6-[3-(4-acetylamino-5-chloro-2-methoxybenzamido)-9-azabicyclo[3.3.1]non-9-yl]hexanoate fumarate Appearance: colorless needles (EtOH)
m.p. 157°–161° C.
Anal. $C_{25}H_{36}ClN_3O_5 \cdot C_4H_4O_4 \cdot 5/4H_2O$
Calcd. C: 55.06; H: 6.77; N, 6.64
Found C: 54.95; H: 6.94; N, 6.72

Example 16: Methyl endo-8-[3-(4-acetylamino-5-chloro-2-methoxybenzamido)-9-azabicyclo[3.3.1]non-9-yl]octanoate Appearance: colorless needles (EtOH)
IR Spectrum $\nu$ (KBr) cm$^{-1}$: 1738, 1704, 1646
NMR Spectrum $\delta$ (CDCl$_3$) ppm: 1.00–2.10(18H,m), 2.28(3H,s), 2.31(2H,t,J=7.5Hz), 2.35–2.55(2H,m), 2.55–2.75(2H,m), 3.10–3.25(2H,m), 3.67(3H,s), 3.98(3H,s), 4.30–4.55(1H,m), 7.55–7.75(1H,m), 7.81(1H,s), 8.21(1H,s), 8.31(1H,s)

High Resolution Mass Spectrum: $C_{27}H_{40}ClN_3O_5$
Calcd. m/z: 521.2657, 523.2627
Found m/z: 521.2642, 523.2617

Example 17: Ethyl endo-3-[3-(4-acetylamino-5-chloro-2-methoxybenzamido)-9-azabicyclo[3.3.1]non-9-yl]propionate sesquifumarate Appearance: colorless needles (EtOH)
m.p. 170°–172° C.
Anal. $C_{23}H_{32}ClN_3O_5 \cdot 3/2C_4H_4O_4$
Calcd. C: 54.42; H: 5.98; N: 6.56
Found C: 54.18; H: 6.06; N: 6.69

Example 18: Ethyl endo-5-[3-(4-acetylamino-5-chloro-2-methoxybenzamido)-9-azabicyclo[3.3.1]non-9-yl]valerate fumarate Appearance: colorless crystals (acetone)
m.p. 127°–129° C.
Anal. $C_{25}H_{36}ClN_3O_5 \cdot C_4H_4O_4 \cdot \frac{1}{2}H_2O$
Calcd. C: 56.26; H: 6.67; N: 6.79
Found C: 56.34; H: 6.72; N: 6.65

Example 19: Methyl endo-7-[3-(4-acetylamino-5-chloro-2-methoxybenzamido)-9-azabicyclo[3.3.1]non-9-yl]heptanoate fumarate Appearance: colorless needles (MeOH-Et$_2$O)
m.p. 124.5°–126° C.
Anal. $C_{26}H_{38}ClN_3O_5 \cdot C_4H_4O_4 \cdot 3/4H_2O$
Calcd. C: 56.51; H: 6.88; N: 6.59
Found C: 56.51; H: 6.82; N: 6.59

Example 20: Ethyl endo-[3-(4-acetylamino-5-chloro-2-ethoxybenzamido)-9-azabicyclo[3.3.1]non-9-yl]acetate Appearance: slightly yellow syrup
IR Spectrum $\nu$ (liq) cm$^{-1}$: 1748, 1704, 1646
NMR Spectrum $\delta$ (CDCl$_3$) ppm: 1.05–1.64(5H,m), 1.75–2.10(3H,m), 2.45–2.65(2H,m), 1.28(3H,t,J=7.0Hz), 1.52(3H,t,J=7.0Hz), 2.27(3H,s), 3.16–3.31(2H,m), 3.49(2H,s), 4.18(2H,q,J=7.0Hz), 4.22(2H,q,J=7.0Hz), 4.37–4.55(1H,m), 7.78(1H,br-s), 7.80–7.94(1H,m), 8.21(1H,s), 8.27(1H,s)

High Resolution Mass Spectrum: $C_{23}H_{32}ClN_3O_5$
Calcd. m/z: 465.2031, 467.2001
Found m/z: 465.2033, 467.2003

Example 21: Ethyl exo-[3-(4-acetylamino-5-chloro-2-methoxybenzamido)-9-azabicyclo[3.3.1]non-9-yl]acetate ½ fumarate
Appearance: colorless needles (MeOH)
IR Spectrum ν (KBr) cm⁻¹: 1738, 1698, 1638
NMR Spectrum δ (DMSO-d₆) ppm: 1.19(3H,t,J=7.0Hz), 1.43–2.05(10H,m), 2.14(3H,s), 2.90–3.00(2H,m), 3.48(2H,s), 3.85(3H,s), 4.08(2H,q,J=7.0Hz), 4.55–4.73(1H,m), 6.61(1H,s), 7.69(1H,s), 7.73(1H,s), 7.70–7.90(1H,m), 9.42 (1H,s)
High Resolution Mass Spectrum: $C_{22}H_{30}ClN_3O_5$
Calcd. m/z: 451.1874, 453.1844
Found m/z: 451.1876, 453.1840

Example 22: Ethyl exo-[3-(4-acetylamino-5-chloro-2-methoxybenzamido)-8-azabicyclo[3.2.1]oct-8-yl]acetate maleate
Appearance: colorless crystals (EtOH)
m.p. 174°–175° C.
Anal. $C_{21}H_{28}ClN_3O_5 \cdot C_4H_4O_4$
Calcd. C: 54.20; H: 5.82; N: 7.58
Found C: 54.03; H: 5.85; N: 7.56

Example 23: Ethyl endo-[3-(4-amino-5-chloro-2-methoxybenzamido)-9-azabicyclo[3.3.1]non-9-yl]acetate
To a solution of 11.0 g of ethyl endo-[3-(4-acetylamino-5-chloro-2-methoxybenzamido)-9-azabicyclo[3.3.1]non-9-yl]acetate in 22 ml of ethanol, 66 ml of 20% hydrogen chloride/ethanol solution was added and the mixture was refluxed for 1 hour. The reaction mixture was concentrated under reduced pressure, and then the residue was dissolved in water and pH was adjusted to 10 with potassium carbonate. Crystals precipitated were collected by filtration and washed with water and then with isopropyl ether to give 8.88 g of pale brown crystals. Recrystallization from ethanol gave colorless crystals,
m.p. 163.5°–164.5° C.
Anal. $C_{20}H_{28}ClN_3O_4$
Calcd. C: 58.60; H: 6.88; N: 10.25
Found C: 58.39; H: 6.84; N: 10.26

In the same manner as Example 23, the compounds of Examples 24 to 33 were obtained.

Example 24: Ethyl endo-4-[3-(4-amino-5-chloro-2-methoxybenzamido)-9-azabicyclo[3.3.1]non-9-yl]butyrate
Appearance: pale orange prisms (EtOH)
m.p. 136.5°–138° C.
Anal. $C_{22}H_{32}ClN_3O_4$
Calcd. C: 60.33; H: 7.36; N: 9.59
Found C: 60.27;.H: 7.41; N: 9.52

Example 25: Ethyl endo-6-[3-(4-amino-5-chloro-2-methoxybenzamido)-9-azabicyclo[3.3.1]non-9-yl]hexanoate
Appearance: colorless prisms (EtOH)
m.p. 122°–123.5° C.
Anal. $C_{24}H_{36}ClN_3O_4$
Calcd. C: 61.86; H: 7.79; N: 9.02
Found C: 61.68; H: 7.80; N: 9.01

Example 26: Ethyl endo-8-[3-(4-amino-5-chloro-2-methoxybenzamido)-9-azabicyclo[3.3.1]non-9-yl]octanoate
Appearance: colorless needles (EtOH)
m.p. 108°–109° C.
Anal. $C_{26}H_{40}ClN_3O_4$
Calcd. C: 63.21; H: 8.16; N: 8.50
Found C: 62.93; H: 8.14; N: 8.46

Example 27: Ethyl endo-3-[3-(4-amino-5-chloro-2-methoxybenzamido)-9-azabicyclo[3.3.1]non-9-yl]propionate
Appearance: pale pink needles (AcOEt)
m.p. 110°–112° C.
Anal. $C_{21}H_{30}ClN_3O_4$
Calcd. C: 59.50; H: 7.13; N: 9.91
Found C: 59.31; H: 7.12; N: 9.89

Example 28: Ethyl endo-5-[3-(4-amino-5-chloro-2-methoxybenzamido)-9-azabicyclo[3.3.1]non-9-yl]valerate
Appearance: colorless crystals (EtOH)
m.p. 126°–128° C.
Anal. $C_{23}H_{34}ClN_3O_4$
Calcd. C: 61.12; H: 7.58; N: 9.30
Found C: 60.85; H: 7.49; N: 9.26

Example 29: Methyl endo-7-[3-(4-amino-5-chloro-2-methoxybenzamido)-9-azabicyclo[3.3.1]non-9-yl]heptanoate
Appearance: colorless prisms (MeOH-Et₂O)
m.p. 144.5°–145.5° C.
Anal. $C_{24}H_{36}ClN_3O_4$
Calcd. C: 61.86; H: 7.79; N: 9.02
Found C: 61.64; H: 7.75; N: 9.06

Example 30: Ethyl endo-[3-(4-amino-5-chloro-2-ethoxybenzamido)-9-azabicyclo[3.3.1]non-9-yl]acetate
Appearance: colorless needles (EtOH)
m.p. 215°–217° C.
Anal. $C_{21}H_{30}ClN_3O_4$
Calcd. C: 59.50; H: 7.13; N: 9.91
Found C: 59.26; H, 7.04; N: 9.87

Example 31: Ethyl exo-[3-(4-amino-5-chloro-2-methoxybenzamido)-9-azabicyclo[3.3.1]non-9-yl]acetate
Appearance: pale pink crystals (iso-PrOH-Et₂O)
m.p. 161°–164° C.
Anal. $C_{20}H_{28}ClN_3O_4 \cdot \tfrac{3}{4}H_2O$
Calcd. C: 56.73; H: 7.02; N: 9.92
Found C: 56.73; H: 6.63; N: 9.96

Example 32: Ethyl endo-[3-(4-amino-5-chloro-2-methoxybenzamido)-8-azabicyclo[3.2.1]oct-8-yl]acetate
Appearance: colorless plates (EtOH)
m.p. 187°–188° C.
Anal. $C_{19}H_{26}ClN_3O_4$
Calcd. C: 57.65; H: 6.62; N: 10.61
Found C: 57.57; H: 6.52; N: 10.42

Example 33: Ethyl exo-[3-(4-amino-5-chloro-2-methoxybenzamido)-8-azabicyclo[3.2.1]oct-8-yl]acetate
Appearance: pale orange prisms (EtOH-Et₂O)
m.p. 188.5°–190° C.
Anal. $C_{19}H_{26}ClN_3O_4$
Calcd. C: 57.65; H: 6.62; N: 10.61
Found C: 57.60; H: 6.57; N: 10.49

Example 34: endo-[3-(4-Amino-5-chloro-2-methoxybenzamido)-9-azabicyclo[3.3.1]non-9-yl]acetic acid hydrochloride
To a suspension of 8.00 g of ethyl endo-[3-(4-amino-5-chloro-2-methoxybenzamido)-9-azabicyclo[3.3.1]non-9-yl]acetate in 80 ml of methanol, 19.5 ml of 2N sodium hydroxide solution was added and the mixture was refluxed for 1 hour. After the reaction mixture was concentrated under reduced pressure, the residue was dissolved in a small volume of water and pH was adjusted to 1 with 10% hydrochloric acid. Crystals precipitated were collected by filtration, washed with water, and then recrystallized from methanol-isopropyl ether to give 5.75 g of colorless powder, m.p. 189°–194° C. (decomp.).

Anal. $C_{18}H_{24}ClN_3O_4 \cdot HCl \cdot H_2O$
Calcd. C: 49.55; H: 6.23; N: 9.63
Found C: 49.38; H: 5.99; N: 9.49

In the same manner as Example 34, the compounds of Examples 35 to 45 were obtained.

Example 35: endo-4-[3-(4-Amino-5-chloro-2-methoxybenzamido)-9-azabicyclo[3.3.1]non-9-yl]butyric acid hydrochloride Appearance: colorless crystals ($H_2O$)
m.p. 166°–167° C.
Anal. $C_{20}H_{28}ClN_3O_4 \cdot HCl \cdot 3/2H_2O$
Calcd. C: 50.74; H: 6.81; N: 8.88
Found C: 50.68; H: 6.66; N: 8.91

Example 36: endo-6-[3-(4-Amino-5-chloro-2-methoxybenzamido)-9-azabicyclo[3.3.1]non-9-yl]hexanoic acid hydrochloride Appearance: colorless crystals ($H_2O$)
m.p. 237°–239° C.
Anal. $C_{22}H_{32}ClN_3O_4 \cdot HCl \cdot 5/4H_2O$
Calcd. C: 53.17; H: 7.20; N: 8.46
Found C: 53.32; H: 7.01; N: 8.48

Example 37: endo-8-[3-(4-Amino-5-chloro-2-methoxybenzamido)-9-azabicyclo[3.3.1]non-9-yl]octanoic acid hydrochloride Appearance: slightly orange crystals ($H_2O$)
m.p. 125°–128° C.
Anal. $C_{24}H_{36}ClN_3O_4 \cdot HCl \cdot 5/4H_2O$
Calcd. C: 54.91; H: 7.58; N: 8.00
Found C: 54.87; H: 7.44; N: 7.98

Example 38: endo-3-[3-(4-Amino-5-chloro-2-methoxybenzamido)-9-azabicyclo[3.3.1]non-9-yl]propionic acid hydrochloride Appearance: pale brown prisms ($H_2O$)
m.p. 157°–160° C.
Anal. $C_{19}H_{26}ClN_3O_4 \cdot HCl \cdot 7/4H_2O$
Calcd. C: 49.20; H: 6.63; N: 9.06
Found C: 49.27; H: 6.41; N: 9.07

Example 39: endo-5-[3-(4-Amino-5-chloro-2-methoxybenzamido)-9-azabicyclo[3.3.1]non-9-yl]valeric acid hydrochloride Appearance: pale pink crystals ($H_2O$)
m.p. 152°–153.5° C.
Anal. $C_{21}H_{30}ClN_3O_4 \cdot HCl \cdot 7/4H_2O$
Calcd. C: 51.27; H: 7.06; N: 8.54
Found C: 51.30; H: 6.89; N: 8.53

Example 40: endo-7-[3-(4-Amino-5-chloro-2-methoxybenzamido)-9-azabicyclo[3.3.1]non-9-yl]heptanoic acid hydrochloride Appearance: colorless needles ($H_2O$)
m.p. 130°–133° C.
Anal. $C_{23}H_{34}ClN_3O_4 \cdot HCl \cdot 2H_2O$
Calcd. C: 52.67; H: 7.49; N: 8.01
Found C: 52.61; H: 7.21; N: 8.14

Example 41: endo-[3-(4-Amino-5-chloro-2-ethoxybenzamido)-9-azabicyclo[3.3.1]non-9-yl]acetic acid hydrochloride Appearance: slightly yellow needles ($H_2O$)
m.p. 216°–220° C. (decomp.)
Anal. $C_{19}H_{26}ClN_3O_4 \cdot HCl \cdot 5/2H_2O$
Calcd. C: 47.80; H: 6.76; N: 8.80
Found C: 48.05; H: 6.41; N: 8.93

Example 42: exo-[3-(4-Amino-5-chloro-2-methoxybenzamido)-9-azabicyclo[3.3.1]non-9-yl]acetic acid Appearance: pale orange crystals (MeOH)
m.p. 250°–252° C. (decomp.)
Anal. $C_{18}H_{24}ClN_3O_4 \cdot \tfrac{3}{4}H_2O$
Calcd. C: 54.68; H: 6.50; N: 10.63
Found C: 54.68; H: 6.25; N: 10.94

Example 43: endo-[3-(4-Amino-5-chloro-2-methoxybenzamido)-8-azabicyclo[3.2.1]oct-8-yl]acetic acid hydrochloride Appearance: slightly yellow needles ($H_2O$)
m.p. 254°–256° C. (decomp.)
Anal. $C_{17}H_{22}ClN_3O_4 \cdot HCl \cdot 3/2H_2O$
Calcd. C: 47.34; H: 6.08; N: 9.74
Found C: 47.36; H: 5.96; N: 9.79

Example 44: endo-4-[3-(4-Amino-5-chloro-2-methoxybenzamido)-8-azabicyclo[3.2.1]oct-8-yl]butyric acid hydrochloride Appearance: colorless crystals ($H_2O$)
m.p. 242°–243° C.
Anal. $C_{19}H_{26}ClN_3O_4 \cdot HCl \cdot 5/4H_2O$
Calcd. C: 50.17; H: 6.54; N: 9.24
Found C: 50.29; H: 6.38; N: 9.23

Example 45: exo-[3-(4-Amino-5-chloro-2-methoxybenzamido)-8-azabicyclo[3.2.1]oct-8-yl]butyric acid Appearance: pale orange crystals (MeOH-$Et_2O$)
m.p. 273°–276° C. (decomp.)
Anal. $C_{17}H_{22}ClN_3O_4$
Calcd. C: 55.51; H: 6.03; N: 11.42
Found C: 55.20; H: 6.05; N: 11.20

Example 46: Ethyl [4-(4-amino-5-chloro-2-methoxybenzamido)piperidino]acetate hydrochloride A mixture of 3.20 g of 4-amino-5-chloro-2-methoxy-N-(4-piperidinyl)benzamide hydrochloride, 1.22 ml of ethyl bromoacetate, 3.04 g of potassium carbonate, and 32 ml of N,N-dimethylformamide was stirred for 2.5 hours with heating at 60° C. The reaction mixture was concentrated under reduced pressure, and then the residue was added with water and extracted with dichloromethane. The extract was washed with saturated aqueous sodium chloride solution, dried over anhydrous sodium sulfate, and then concentrated under reduced pressure to give brown oil. The result was converted to the hydrochloride by an ordinary method to afford 3.31 g of pale yellow crystals. Recrystallization from ethanol gave colorless plates, m.p. 196.5°–198.5° C.

Anal. $C_{17}H_{24}ClN_3O_4 \cdot HCl$
Calcd. C: 50.25; H: 6.20; N: 10.34
Found C: 49.98; H: 6.23; N: 10.36

In the same manner as Example 46, the compounds of Examples 47–57 were obtained.

Example 47: Ethyl 4-[4-(4-amino-5-chloro-2-methoxybenzamido)piperidino]butyrate hydrochloride Appearance: slightly brown columns (EtOH)
m.p. 188.5°–191.5° C.
Anal. $C_{19}H_{28}ClN_3O_4 \cdot HCl$
Calcd. C: 52.54; H: 6.73; N: 9.67
Found C: 52.18; H: 6.66; N: 9.75

Example 48: Methyl 6-[4-(4-amino-5-chloro-2-methoxybenzamido)piperidino]hexanoate hydrochloride Appearance: slightly brown needles (MeOH)
m.p. 208.5°–210.5° C.
Anal. $C_{20}H_{30}ClN_3O_4 \cdot HCl \cdot 5/4H_2O$
Calcd. C: 51.01; H: 7.17; N: 8.92
Found C: 51.06; H: 7.03; N: 8.99

Example 49: Ethyl 3-[4-(4-amino-5-chloro-2-methoxybenzamido)piperidino]propionate Appearance: colorless needles (acetone-$Et_2O$)
m.p. 116°–117.5° C.
Anal. $C_{18}H_{26}ClN_3O_4$
Calcd. C: 56.32; H: 6.83; N: 10.95

Found C: 56.28; H: 6.74; N: 10.87

Example 50: Ethyl 5-[4-(4-amino-5-chloro-2-methoxybenzamido)piperidino]valerate hydrochloride
Appearance: colorless crystals (EtOH)
m.p. 202°–203.5° C.
Anal. $C_{20}H_{30}ClN_3O_4 \cdot HCl \cdot \frac{1}{4}H_2O$
Calcd. C: 53.04; H: 7.01; N: 9.28
Found C: 52.99; H: 6.95; N: 9.21

Example 51: Ethyl 2-[4-(4-amino-5-chloro-2-methoxybenzamido)piperidino]propionate fumarate
Appearance: slightly yellow crystals (EtOH)
m.p. 158°–159° C.
Anal. $C_{18}H_{26}ClN_3O_4 \cdot C_4H_4O_4$
Calcd. C: 52.85; H: 6.05; N: 8.40
Found C: 52.67; H: 5.94; N: 8.39

Example 52: Ethyl cis-[4-(4-amino-5-chloro-2-methoxybenzamido)-3-methoxypiperidino]acetate hydrochloride
Appearance: colorless needles (MeOH)
m.p. 225°–226° C.
Anal. $C_{18}H_{26}ClN_3O_5 \cdot HCl \cdot \frac{1}{4}H_2O$
Calcd. C: 49.04; H: 6.29; N: 9.53
Found C: 48.89; H: 6.14; N: 9.44

Example 53: Ethyl cis-4-[4-(4-amino-5-chloro-2-methoxybenzamido)-3-methoxypiperidino]butyrate hydrochloride
Appearance: colorless crystals (EtOH)
m.p. 218°–219.5° C.
Anal. $C_{20}H_{30}ClN_3O_5 \cdot HCl$
Calcd. C: 51.73; H: 6.73; N: 9.05
Found C: 51.45; H: 6.64; N: 8.98

Example 54: Ethyl cis-6-[4-(4-amino-5-chloro-2-methoxybenzamido)-3-methoxypiperidino]hexanoate hydrochloride
Appearance: colorless crystals (EtOH)
m.p. 207°–208.5° C.
Anal. $C_{22}H_{34}ClN_3O_5 \cdot HCl \cdot \frac{1}{4}H_2O$
Calcd. C: 53.17; H: 7.20; N: 8.46
Found C: 52.95; H: 7.09; N: 8.35

Example 55: Ethyl [2-[(4-amino-5-chloro-2-methoxybenzamido)methyl]morpholino]acetate hydrochloride
Appearance: pale yellow crystals (H₂O)
m.p. 203°–204° C.
Anal. $C_{17}H_{24}ClN_3O_5 \cdot HCl$
Calcd. C: 48.35; H: 5.97; N: 9.95
Found C: 48.12; H: 6.03; N: 9.75

Example 56: Ethyl 4-[2-[(4-amino-5-chloro-2-methoxybenzamido)methyl]morpholino]butyrate hydrochloride
Appearance: pale yellow crystals (EtOH)
m.p. 196°–197° C.
Anal. $C_{19}H_{28}ClN_3O_5 \cdot HCl \cdot \frac{1}{2}H_2O$
Calcd. C: 49.68; H: 6.58; N: 9.15
Found C: 49.59; H: 6.65; N: 9.10

Example 57: Ethyl [3-[(4-amino-5-chloro-2-methoxybenzamido)methyl]pyrrolidin-1-yl]acetate
Appearance: pale yellow oil
IR Spectrum ν (liq.) cm⁻¹: 1744, 1632
NMR Spectrum δ (CDCl₃) ppm: 1.27(3H,t,J=7.0Hz), 1.46–1.69(1H,m), 1.93–2.14(1H,m), 2.38–2.99(5H,m), 3.24–3.54(4H,m), 3.89(3H,s), 4.18(2H,q,J=7.0Hz), 4.39(2H,br-s), 6.29(1H,s), 7.81(1H,br-s), 8.09(1H,s) High Resolution Mass Spectrum: $C_{17}H_{24}ClN_3O_4$
Calc. m/z: 369.1455, 371.1426
Found m/z: 369.1466, 371.1439

Example 58: [4-[(4-Amino-5-chloro-2-methoxybenzamido)piperidino]acetic acid hydrochloride To a suspension of 2.23 g of ethyl [4-[(4-amino-5-chloro-2-methoxybenzamido)piperidino]acetate in 22 ml of methanol, 9,86 ml of 2N sodium hydroxide solution was added and the mixture was refluxed for 1 hour. After methanol was removed by distillation under reduced pressure, 10% hydrochloric acid was added to the residue and pH was adjusted to 2. After the mixture was cooled to 5° C., crystals precipitated were collected by filtration and washed with water to give 1.47 g of pale brown crystals. Recrystallization from water gave pale yellow prisms, m.p. 248°–251° C. (decomp.).
Anal. $C_{15}H_{20}ClN_3O_4 \cdot HCl \cdot \frac{1}{4}H_2O$
Calcd. C: 47.07; H: 5.66; N: 10.98
Found C: 47.34; H: 5.58; N: 11.08

In the same manner as Example 58, the compounds of Examples 59–68 were obtained.

Example 59: 4-[4-(4-Amino-5-chloro-2-methoxybenzamido)piperidino]butyric acid hydrochloride
Appearance: pale yellow prisms (H₂O)
m.p. 228.5°–231.5° C.
Anal. $C_{17}H_{24}ClN_3O_4 \cdot HCl \cdot H_2O$
Calcd. C: 48.12; H: 6.41; N: 9.90
Found C: 47.97; H: 6.34; N: 10.12

Example 60: 6-[4-(4-Amino-5-chloro-2-methoxybenzamido)piperidino]hexanoic acid hydrochloride
Appearance: slightly brown prisms (H₂O)
m.p. 223°–225° C.
Anal. $C_{19}H_{28}ClN_3O_4 \cdot HCl \cdot H_2O$
Calcd. C: 50.45; H: 6.91; N: 9.29
Found C: 50.33; H: 6.84; N: 9.25

Example 61: 3-[4-(4-Amino-5-chloro-2-methoxybenzamido)piperidino]propionic acid hydrochloride
Appearance: colorless needles (H₂O)
m.p. 218°–219.5° C.
Anal. $C_{16}H_{22}ClN_3O_4 \cdot HCl$
Calcd. C: 48.99; H: 5.91; N: 10.71
Found C: 48.80; H: 5.84; N: 10.68

Example 62: 5-[4-(4-Amino-5-chloro-2-methoxybenzamido)piperidino]valeric acid hydrochloride
Appearance: colorless crystals (H₂O)
m.p. 226°–227.5° C.
Anal. $C_{18}H_{26}ClN_3O_4 \cdot HCl \cdot H_2O$
Calcd. C: 49.32; H: 6.67; N: 9.59
Found C: 49.18; H: 6.45; N: 9.54

Example 63: 2-[4-(4-Amino-5-chloro-2-methoxybenzamido)piperidino]propionic acid
Appearance: pale yellow crystals (H₂O)
m.p. 246°–247° C.
Anal. $C_{16}H_{22}ClN_3O_4 \cdot 5/4H_2O$
Calcd. C: 50.79; H: 6.53; N: 11.11
Found C: 50.59; H: 6.25; N: 11.06

Example 64: cis- [4-(4-Amino-5-chloro-2-methoxybenzamido)-3-methoxypiperidino] acetic acid
Appearance: colorless needles (H₂O)
m.p. 230°–233° C. (decomp.)
Anal. $C_{16}H_{22}ClN_3O_5 \cdot 5/2H_2O$
Calcd. C: 46.10; H: 6.53; N: 10.08
Found C: 46.18; H: 6.57; N: 10.00

Example 65: cis-4-[4-(4-Amino-5-chloro-2-methoxybenzamido)-3-methoxypiperidino]butyric acid hydrochloride
Appearance: colorless needles (H₂O)
m.p. 232°–234.5° C. (decomp.)
Anal. $C_{18}H_{26}ClN_3O_5 \cdot HCl \cdot \frac{1}{4}H_2O$
Calcd. C: 49.04; H: 6.29; N: 9.53
Found C: 49.03; H: 6.19; N: 9.77

Example 66: cis-6-[4-(4-Amino-5-chloro-2-methoxybenzamido)-3-methoxypiperidino]hexanoic acid hydrochloride
Appearance: colorless prisms (H₂O)
m.p. 232.5°–235.5° C. (decomp.)
Anal. $C_{20}H_{30}ClN_3O_5 \cdot HCl$
Calcd. C: 51.73; H: 6.73; N: 9.05
Found C: 51.52; H: 6.62; N: 8.90

Example 67: [2-[(4-Amino-5-chloro-2-methoxybenzamido)methyl]morpholino]acetic acid
Appearance: slightly yellow crystals (MeOH)
m.p. 208°–210° C.
Anal. $C_{15}H_{20}ClN_3O_5$
Calcd. C: 50.35; H: 5.63; N: 11.74
Found C: 50.04; H: 5.53; N: 11.63

Example 68: 4-[2-[(4-Amino-5-chloro-2-methoxybenzamido)methyl]morpholino]butyric acid
Appearance: colorless needles (EtOH)
m.p. 194°–195° C.
Anal. $C_{17}H_{24}ClN_3O_5$
Calcd. C: 52.92; H: 6.27; N: 10.89
Found C: 52.60; H: 6.09; N: 10.83

| Formulation 1 | |
| --- | --- |
| Compound of Example 23 | 5 mg |
| Lactose | suitable amount |
| Cornstarch | 15 mg |
| Magnesium Stearate | 1 mg |
| | 80 mg |
| Formulation 2 | |
| Compound of Example 23 | 5 mg |
| Lactose | siutable amount |
| Cornstarch | 15 mg |
| Magnesium Stearate | 1 mg |
| Hydroxypropylmethylcellulose | 4 mg |
| Polyethylene glycol 6000 | 0.5 mg |
| Titanium Oxide | 0.5 mg |
| | 100 mg |
| Formulation 3 | |
| Compound of Example 23 | 10 mg |
| Lactose | siutable amount |
| D-mannitol | 500 mg |
| Hydroxypropylcellulose | 20 mg |
| Talc | 2 mg |
| | 1,000 mg |
| Formulation 4 | |
| Compound of Example 23 | 5 mg |
| Citric Acid | 0.5 mg |
| Glucose | 50 mg |
| Sodium Hydroxide | siutable amount |
| Distilled Water for Injection | siutable amount |
| | 1 ml |
| Formulation 5 | |
| Compound of Example 23 | 5 mg |
| Hard Fat | 1,295 mg |
| | 1,300 mg |

Industrial Applicability

As explained above, the novel benzamide derivatives of the present invention represented by formula (I) have excellent gastrointestinal stimulating activity and antiemetic activity and thus are useful for the treatment of gastrointestinal diseases.

What is claimed is:

1. A benzamide derivative represented by the following formula:

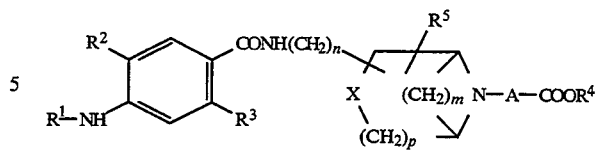

wherein, $R^1$ represents a hydrogen atom or a lower alkanoyl group; $R^2$ represents a hydrogen atom or a halogen atom; $R^3$ represents a lower alkoxy group; $R^4$ represents a hydrogen atom or a lower alkyl group; $R^5$ represents a hydrogen atom, a lower alkyl group, or a lower alkoxy group; A represents $C_1$–$C_7$ alkylene group which may optionally be substituted with a lower alkyl group; X represents a methylene group, an oxygen atom, or a sulfur atom; m represents an integer of from 1 to 3; n represents an integer of from 0 to 3; and p represents an integer of from 0 to 2, and a pharmacologically acceptable salt thereof.

2. Ethyl endo-[3-(4-amino-5-chloro-2-methoxybenzamido)-9-azabicyclo[3.3.1]non-9-yl]acetate and a pharmacologically acceptable salt thereof.

3. Endo-[3-(4-amino-5-chloro-2-methoxybenzamido)-9-azabicyclo[ 3.3.1]non-9-yl]acetic acid and a pharmacologically acceptable salt thereof.

4. Ethyl endo-4-[3-(4-amino-5-chloro-2-methoxybenzamido)-9-azabicyclo[3.3.1]non-9-yl]butyrate and a pharmacologically acceptable salt thereof.

5. Endo-4-[3-(4-amino-5-chloro-2-methoxybenzamido)-9-azabicyclo[3.3.1]non-9-yl ]butyric acid and a pharmacologically acceptable salt thereof.

6. Ethyl endo-[3-(4-amino-5-chloro-2-methoxybenzamido)-8-azabicyclo[3.2.1]oct-8-yl]acetate and a pharmacologically acceptable salt thereof.

7. Endo-[3-(4-amino-5-chloro-2-methoxybenzamido)-8-azabicyclo[3.2.1]oct-8-yl]acetic acid and a pharmacologically acceptable salt thereof.

8. Ethyl endo-4-[3-(4-amino-5-chloro-2-methoxybenzamido)-8-azabicyclo[3.2.1]oct-8-yl]butyrate and a pharmacologically acceptable salt thereof.

9. Endo-4-[3-(4-amino-5-chloro-2-methoxybenzamido)-8-azabicyclo[3.2.1]oct-8-yl ]butyric acid and a pharmacologically acceptable salt thereof.

10. A pharmaceutical composition comprising a benzamide derivative represented by the following formula:

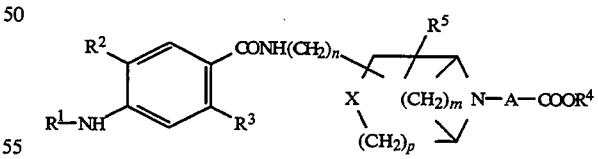

wherein $R^1$ represents a hydrogen atom or a lower alkanoyl group; $R^2$ represents a hydrogen atom or a halogen atom; $R^3$ represents a lower alkoxy group; $R^4$ represents a hydrogen atom or a lower alkyl group; $R^5$ represents a hydrogen atom, a lower alkyl group, or a lower alkoxy group; A represents $C_1$–$C_7$ alkylene group which may optionally be substituted with a lower alkyl group; X represents a methylene group, an oxygen atom, or a sulfur atom; m represents an integer of from 1 to 3; n represents an integer of from 0 to 3; and p represents an integer of from 0 to 2 or a pharmacologically acceptable salt thereof as an active ingredient.

11. The composition according to claim 10, which is useful for the treatment of gastrointestinal diseases.

12. A method for treatment of gastrointestinal diseases comprising the step of administering to a patient an effective amount of a benzamide derivative represented by the following formula:

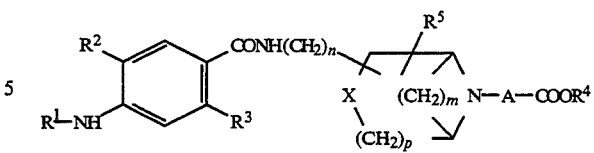

wherein $R^1$ represents a hydrogen atom or a lower alkanoyl group; $R^2$ represents a hydrogen atom or a halogen atom; $R^3$ represents a lower alkoxy group; $R^4$ represents a hydrogen atom or a lower alkyl group; $R^5$ represents a hydrogen atom, a lower alkyl group, or a lower alkoxy group; A represents $C_1$-$C_7$ alkylene group which may optionally be substituted with a lower alkyl group; X represents a methylene group, an oxygen atom, or a sulfur atom; m represents an integer of from 1 to 3; n represents an integer of from 0 to 3; and p represents an integer of from 0 to 2 or a pharmacologically acceptable salt thereof.

* * * * *

UNITED STATES PATENT AND TRADEMARK OFFICE
CERTIFICATE OF CORRECTION

PATENT NO.    : 5,395,832

DATED         : March 7, 1995

INVENTOR(S)   : ITO, et al.

It is certified that error appears in the above-identified patent and that said Letters Patent is hereby corrected as shown below:

Column 6, line 55, change "cis-4-[4-i" and insert -- cis-4- [4-(4--.

Column 15, line 19, change "3.2%" and insert -- 32% --.

Signed and Sealed this

Nineteenth Day of March, 1996

Attest:

BRUCE LEHMAN

Attesting Officer        Commissioner of Patents and Trademarks